(12) United States Patent
Prinstil et al.

(10) Patent No.: US 8,539,828 B2
(45) Date of Patent: Sep. 24, 2013

(54) MAGNETOSTRICTIVE LIQUID DENSITY DETECTOR

(75) Inventors: Ambroise Prinstil, East Hartford, CT (US); Joseph Tessitore, Orange, CT (US)

(73) Assignee: Veeder-Root Company, Simsbury, CT (US)

( * ) Notice: Subject to any disclaimer, the term of this patent is extended or adjusted under 35 U.S.C. 154(b) by 575 days.

(21) Appl. No.: 12/652,607

(22) Filed: Jan. 5, 2010

(65) Prior Publication Data
US 2010/0170338 A1 Jul. 8, 2010

Related U.S. Application Data

(60) Provisional application No. 61/142,666, filed on Jan. 6, 2009.

(51) Int. Cl.
*G01F 23/38* (2006.01)

(52) U.S. Cl.
USPC .......................................................... 73/305

(58) Field of Classification Search
USPC ................ 73/305, 309, 311, 313, 314, 319
See application file for complete search history.

(56) References Cited

U.S. PATENT DOCUMENTS

| | | | |
|---|---|---|---|
| 4,155,254 A | 5/1979 | Colditz | 73/447 |
| 4,972,710 A | 11/1990 | Uhlarik et al. | 73/292 |
| 7,278,311 B1 | 10/2007 | Demin | 73/322.5 |
| 7,403,860 B2 | 7/2008 | Hart | 702/25 |
| 7,454,969 B2 | 11/2008 | Hart | |
| 2006/0169039 A1 | 8/2006 | Zalenski et al. | 73/290 R |
| 2006/0248952 A1 | 11/2006 | Jarvie | 73/444 |
| 2006/0266113 A1 | 11/2006 | Hart | |
| 2009/0265132 A1 | 10/2009 | Schrittenlacher | 702/137 |

FOREIGN PATENT DOCUMENTS

| | | |
|---|---|---|
| GB | 937713 A | 9/1963 |
| WO | 2008104967 A2 | 9/2008 |

OTHER PUBLICATIONS

International Search Report and Written Opinion of the International Searching Authority for PCT/US2010/020228, dated Mar. 15, 2010.
Office Action dated Oct. 31, 2012 for co-pening Chinese Patent Application No. 201080010566.2.
Office Action dated Feb. 8, 2013 for co-pending Russian Patent Application No. 201101054.

*Primary Examiner* — Peter Macchiarolo
*Assistant Examiner* — Tamiko Bellamy
(74) *Attorney, Agent, or Firm* — Nelson Mullins Riley & Scarborough LLP

(57) ABSTRACT

A fluid level probe for use in a tank containing a first fluid, including a probe shaft, a first float with a first magnet that is slidably disposed for movement along the probe shaft and adapted to float at the top surface of the first fluid, a second float with a first magnet that is slidably disposed for movement along the probe shaft beneath the first float and adapted to float within the first fluid, and electronics adapted to determine a first distance between the first magnet of the first float and the first magnet of the second float which is used to determine a first density of the first fluid.

29 Claims, 18 Drawing Sheets

MAGNETOSTRICTIVE LIQUID DENSITY DETECTOR

CLAIM OF PRIORITY

The present application claims priority to U.S. Provisional Patent Application Ser. No. 61/142,666, filed Jan. 6, 2009, entitled Magnetostrictive Liquid Density Detector, the entire disclosure of which is incorporated by reference herein.

FIELD OF THE INVENTION

The present invention relates to an apparatus and method used in a fuel storage tank that can be used to determine the density of the fuel stored within the fuel storage tank.

BACKGROUND OF THE INVENTION

This application incorporates herein by reference in its entirety the disclosures of U.S. Pat. No. 7,403,860, issued Jul. 22, 2008, and U.S. Published Application No. 2006/0169039, published Aug. 3, 2006.

Fueling environments typically store fuel in large storage tanks located beneath the ground, sometimes referred to as "underground storage tanks" (UST). To comply with environmental laws, rules, and regulations, these storage tanks may be double-walled and equipped with various leak detection sensors and inventory reconciliation systems. One popular leak detection sensor is sold by Veeder-Root Company of 125 Powder Forest Drive, Simsbury, Conn. 06070, the assignee of the present application, under the name "The MAG Plus Inventory Measurement Probe" (Mag Probe). This probe is typically matched with a tank monitor, such as the TLS-350R, also sold by Veeder-Root Company. Such probes measure a height of fuel within the storage tank and may optionally measure a height of water (if present). The measurements are reported to the tank monitor for usage by the operator of the fueling environment to evaluate and reconcile fuel inventory and/or detect leaks, as is well understood.

While the United States has many rules and regulations relating to leak monitoring within fueling environments, other locales have additional requirements for fueling environments. For example, countries such as India and Russia have seen a rise in fraud at fueling environments, and have consequently taken steps to combat such fraud. Specifically, these countries have become aware that dilution of the fuel within storage tanks may be used as a technique to defraud a customer. One way in which the diluted fuel is created is through the addition of alcohol to the fuel storage tank. The alcohol allows the water at the bottom of the fueling tank to mix with the fuel, and the diluted mixture is then dispensed as normal through the fuel dispensers.

To combat this fraud, some governments have mandated that fuel density be measured. If the density is outside of a predetermined allowable range, it may be inferred that the fuel has been adulterated. Even if some countries or governments do not have such legislation requiring measurement of fuel density, some fuel distribution companies that operate service stations may nonetheless find it desirable to monitor the density of their fuels for quality control purposes.

Density measurements also assist in calculation of the mass of fluid within a storage container. Differences in mass may be used to perform leak detection for fluids in situations where normal volume detection techniques are inadequate (e.g., waste oil storage containers). These situations create additional demand for density measuring devices.

SUMMARY OF THE INVENTION

One embodiment of the present invention provides a fluid level probe for use in a tank containing a first fluid, including a probe shaft with a top end and a bottom end. A first float carrying a first magnet is slidably disposed for movement along the probe shaft and adapted to float at the top surface of the first fluid and a second float carrying a first magnet is slidably disposed for movement along the probe shaft beneath the first float and adapted to float within the first fluid such that there is magnetic repulsion between the first magnet of the first float and the first magnet of the second float. Electronics are operative to determine a first distance between the first magnet of the first float and the first magnet of the second float.

Another embodiment provides a fluid level probe for use in a tank containing a first fluid and a second fluid forming an interface therebetween. The fluid level probe includes a probe shaft with a top end and a bottom end. A first float carrying a first magnet is slidably disposed for movement along the probe shaft and adapted to float at the interface between the first fluid and the second fluid and a second float carrying a first magnet is slidably disposed for movement along the probe shaft above the first float and adapted to float within the first fluid such that there is magnetic repulsion between the first magnet of the first float and the first magnet of the second float. Electronics are operative to determine a first distance between the first magnet of the first float and the first magnet of the second float.

Yet another embodiment provides a fluid level probe for use in a tank containing a first fluid including a probe shaft with a top end and a bottom end. A first float carrying a first magnet and a second magnet is slidably disposed for movement along the probe shaft and a second float carrying a first magnet is slidably disposed for movement along the probe shaft between the first magnet and the second magnet of the first float and adapted to float within the first fluid such that there is magnetic repulsion between the first magnet of the first float and the first magnet of the second float and also between the second magnet of the first float and the first magnet of the second float. Electronics are operative to determine a first density of the first fluid adjacent the second float based on spacing between the first magnet and the first float and the first magnet of the second float and between the second magnet of the first float and the first magnet of the second float.

Another embodiment provides a fluid level probe for use in a tank containing a first fluid, including a probe shaft with a top end and a bottom end, a first repulsion magnet and a second repulsion magnet being disposed at fixed positions along the probe shaft, and a first float carrying a first magnet that is slidably disposed for movement along the probe shaft between the first repulsion magnet and the second repulsion magnet and adapted to float within the first fluid such that there is magnetic repulsion between the first magnet of the first float and the first repulsion magnet and also between the first magnet of the first float and the second repulsion magnet. Electronics are operative to determine at least a first distance between one of the first repulsion magnet and the second repulsion magnet and the first magnet of the first float.

Yet another embodiment provides an apparatus for determining density of a fluid including a first magnet, a float carrying a second magnet oriented such that there is magnetic repulsion between the first magnet and the second magnet, and structure constraining movement of the float toward and away from the first magnet as the density of the fluid changes.

Electronics are operative to determine the density of the fluid utilizing spacing between the first and second magnets.

Another embodiment provides a method of determining the density of a fluid, including providing a probe shaft including a top end and a bottom end; providing a first float, the first float being slidably disposed for movement along the probe shaft and float at a top surface of the fluid; providing a second float, the second float being slidably disposed for movement along the probe shaft beneath the first float and adapted to float within the fluid; determining a first position of the first float relative to the probe shaft; determining a second position of the second float relative to the probe shaft; determining a first distance that exists between the first position and the second position; and determining a first density of the fluid adjacent the top surface by utilizing the first distance.

Yet another embodiment provides a method of determining the density of a fluid dispersed in a tank with a fluid level probe including a probe shaft, a first float and a second float, including determining a first position of the first float relative to the probe shaft; determining a second position of the second float relative to the probe shaft; determining a first distance between the first position and the second position; and utilizing the first distance to determine a first density of the fluid adjacent the first float and the second float.

Other objects, features and aspects for the present invention are discussed in greater detail below. The accompanying drawings are incorporated in and constitute a part of this specification, and illustrate one or more embodiments of the invention. These drawings, together with the description, serve to explain the principles of the invention.

BRIEF DESCRIPTION OF THE DRAWINGS

A full and enabling disclosure of the present invention, including the best mode thereof, to one of ordinary skill in the art, is set forth more particularly in the remainder of this specification, including reference to the accompanying drawings, in which.

Figure 1:
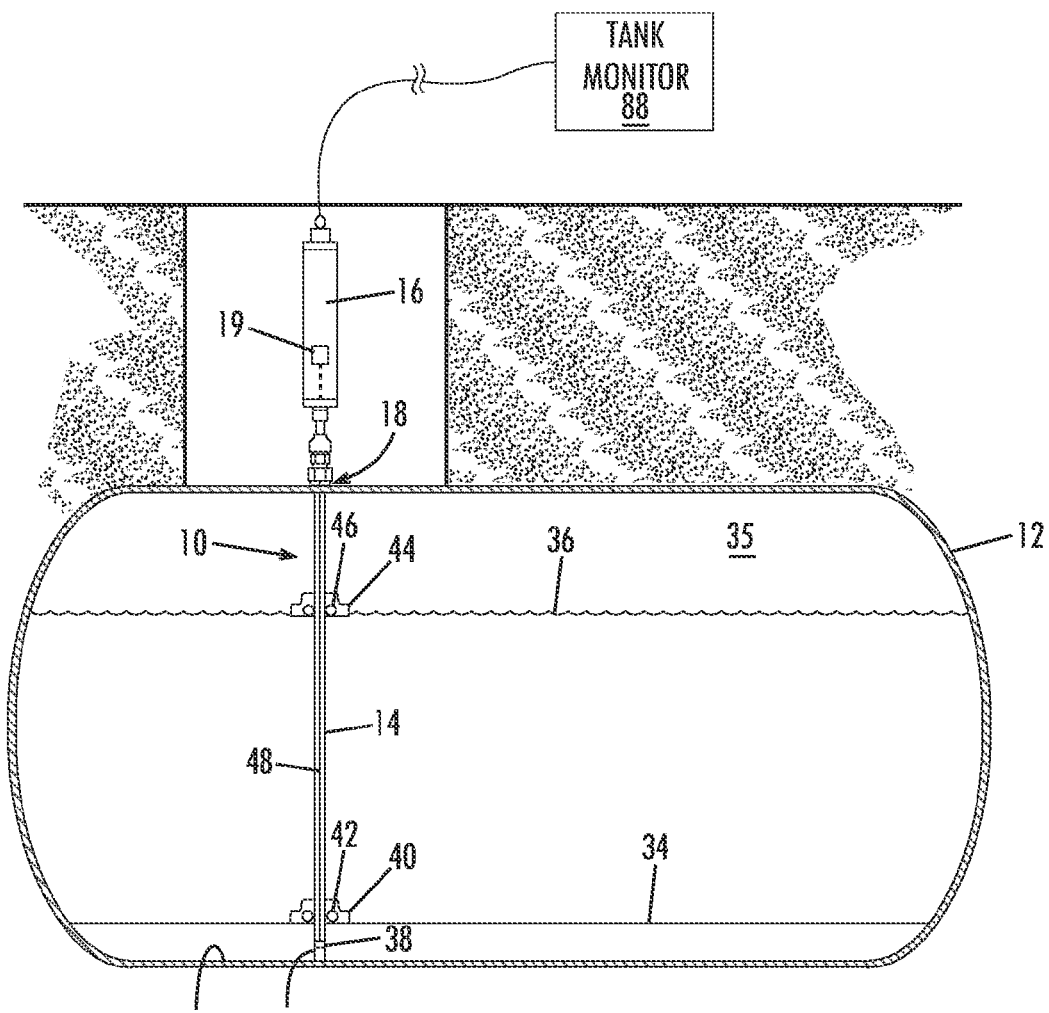
FIG. 1 illustrates a conventional magnetostrictive probe positioned in a fuel storage tank.

Repeat use of reference characters in the present specification and drawings is intended to represent same or analogous features or elements of the invention.

DETAILED DESCRIPTION OF THE PREFERRED EMBODIMENTS

The embodiments set forth below represent the necessary information to enable those skilled in the art to practice the invention and illustrate the best mode of practicing the invention. Upon reading the following description in light of the accompanying drawing figures, those skilled in the art will understand the concepts of the invention and will recognize applications of these concepts not particularly addressed herein. It should be understood that these concepts and applications fall within the scope of the disclosure and the accompanying claims.

Embodiments of the present invention provide a fuel level probe that measures fuel density as well as fuel height in a fuel storage tank. An exemplary fuel level probe is a magnetostrictive probe which has a probe shaft inserted into and fixed with respect to the storage tank. The probe has a reference magnet positioned proximate to a terminal end of the probe shaft. A water level float, typically an annular float, is positioned on the probe shaft and floats at the level of the water-fuel interface. A water level magnet is associated with the water level float so that the level of the water in the fuel storage tank can be ascertained.

A fuel level float, also generally an annular float, is positioned on the probe shaft and floats at the air-fuel interface. A fuel level magnet is associated with the fuel level float so that the level of the fuel in the fuel storage tank can be ascertained. The water level and fuel level floats move freely up and down the probe shaft as the respective levels of fluids (water and fuel) change.

To determine the fuel level and the water level within the fuel storage tank, the probe sends an electric current down a magnetostrictive wire within the probe shaft. The current in the magnetostrictive wire interacts with the magnets and introduces torsional wave reflections in the wire which are detected by a sensor in the probe. The time elapsed between the signal generation and the arrival of the reflections may be used to measure the distance from the sensor to the respective magnet. In accordance with the present invention, the probe is also adapted to determine fuel density. The probe may either perform the calculations to arrive at the density of the fuel or may report its measurements to a tank monitor or other controller so that the controller may perform the calculations to determine the density of the fuel. The density of other fluids may also be measured with the probe of the present invention and the invention is not strictly limited to use in a fueling environment.

A discussion of a conventional magnetostrictive fuel level probe 10 (hereinafter "probe") is first presented herein with reference to FIG. 1. The discussion of preferred embodiments of the present invention follows beginning with reference to FIG. 2 below.

Thus, referring now to FIG. 1, the probe 10 is a magnetostrictive probe, such as the MAG PROBE™ magnetostrictive probe sold by the assignee of the present invention, namely Veeder-Root Company of 125 Powder Forest Drive, Simsbury, Conn. 06070. The probe 10 is positioned partially in a fuel storage tank 12. Specifically, the probe includes a probe shaft 14 that extends into the fuel storage tank 12 while a canister 16 is positioned outside of the fuel storage tank 12. As shown, the canister 16 is attached to the probe shaft 14 via fittings 18. However, fittings may or may not be used depending on the application. The canister 16 includes electronics 19, which enable operation of the probe 10 as further explained below.

In use, most fuel storage tanks, such as fuel storage tank 12, have a small amount of water therein. This water collects at the bottom of the fuel storage tank 12, forming a water-fuel interface 34. The fuel sits on top of the water and has an air-fuel interface 36 at the ullage 35 of the fuel storage tank 12. The probe shaft 14 extends through both interfaces 34 and 36. The probe shaft 14 has a reference magnet 38 positioned proximate a terminal end 28 of the probe shaft 14 at a fixed, known distance from the terminal end 28. The reference magnet 38 may be positioned internal to the probe shaft 14 as is conventional, or externally in a boot (not shown) that slips over the end of the probe shaft 14. A water level float 40, typically an annular float, is positioned on the probe shaft 14 and floats at the level of the water-fuel interface 34. A water level magnet 42 is associated with the water level float 40 so that the level of the water in the fuel storage tank 12 can be ascertained.

A fuel level float 44, also generally an annular float, is positioned on the probe shaft 14 and floats at the air-fuel interface 36. A fuel level magnet 46 is associated with the fuel level float 44 so that the level of the fuel in the fuel storage tank 12 can be ascertained. It should be appreciated that the floats 40 and 44 move freely up and down the probe shaft 14 as the respective levels of fluids (water and fuel) change. Likewise, the buoyancy of the floats 40 and 44 is determined by the fluid on which they will be floating. Such parameters are conventional and well understood by someone of ordinary skill in the art. However, the interested reader is directed to the MAG 1 & 2 PLUS! PROBES ASSEMBLY GUIDE, published by Veeder-Root, which is available online at http://www.veeder.com/page/search.html?keywords=mag+probe. The ASSEMBLY GUIDE is hereby incorporated by reference in its entirety.

To determine the fuel level and the water level within the fuel storage tank 12, the probe 10 generates an electric current with a current source within the electronics 19 positioned in the canister 16 and sends the electric current down a magnetostrictive wire 48 in the probe shaft 14. Then, the probe 10 detects torsional wave reflections induced by the magnets 42 and 46 of the floats 40 and 44, respectively, and the reference magnet 38. The torsional wave reflections are detected with a detector such as a sensing coil (not shown explicitly) of the electronics 19.

The first reflection to arrive at the detector is a reflection from the fuel level magnet 46 associated with the fuel level float 44. The second reflection to arrive at the detector is a reflection from the water level magnet 42 associated with the water level float 40. A third reflection arrives from the reference magnet 38. Since the speed of the torsional wave in the magnetostrictive wire 48 is known (typically about 3000 m/s), it is possible to calculate the distance between the detector and the magnet that induced the torsional wave. The detector thus measures the time elapsed between the origination of the pulse and the arrival of each torsional wave reflection. If the distance from the detector to a particular magnet is known, it is a well known exercise to determine the level of that particular magnet within the fuel storage tank 12.

Alternatively, the difference in arrival times of torsional waves is used to measure the distance between the level magnets and the reference magnet 38. That is, the distance from the bottom 30 to the reference magnet 38 (the height of the reference magnet) is known. By measuring the time difference between arrival of torsional waves from, for example, the water level magnet 42 and the reference magnet 38, the distance between the two magnets 38 and 42 may be determined. Specifically, the velocity of the torsional wave is multiplied by the time, and a distance is generated. This distance is added to the height of the reference magnet and from this calculation, the height of the water level magnet 42 is determined. Similar calculations may be made for the fuel level magnet 46. Put another way, the heights of the magnets relative to the bottom of the fuel storage tank 12 are determinable.

The probe 10 reports the measured reflections to a tank monitor 88, such as the TLS-350R manufactured and sold by Veeder-Root Company. The tank monitor 88 uses the data from the probe 10, and specifically, the measured reflections to determine the level and thus, the volume of fuel, within the fuel storage tank 12. For example, the tank monitor 88 may determine a volume of fuel within the fuel storage tank from the height of the fuel level, as determined by the height of the fuel level float 44 (and as measured by the first reflection or it's relationship to the reflection of reference magnet 38). From this height, a conventional tank strapping algorithm or other conventional technique may be applied, as is well understood in the art, to convert the fuel level to arrive at the volume of fuel within the fuel storage tank 12. For more information on the operation of a magnetostrictive fuel level probe, the interested reader is referred to U.S. Pat. No. 5,076,100, which is hereby incorporated by reference in its entirety.

Figure 2:
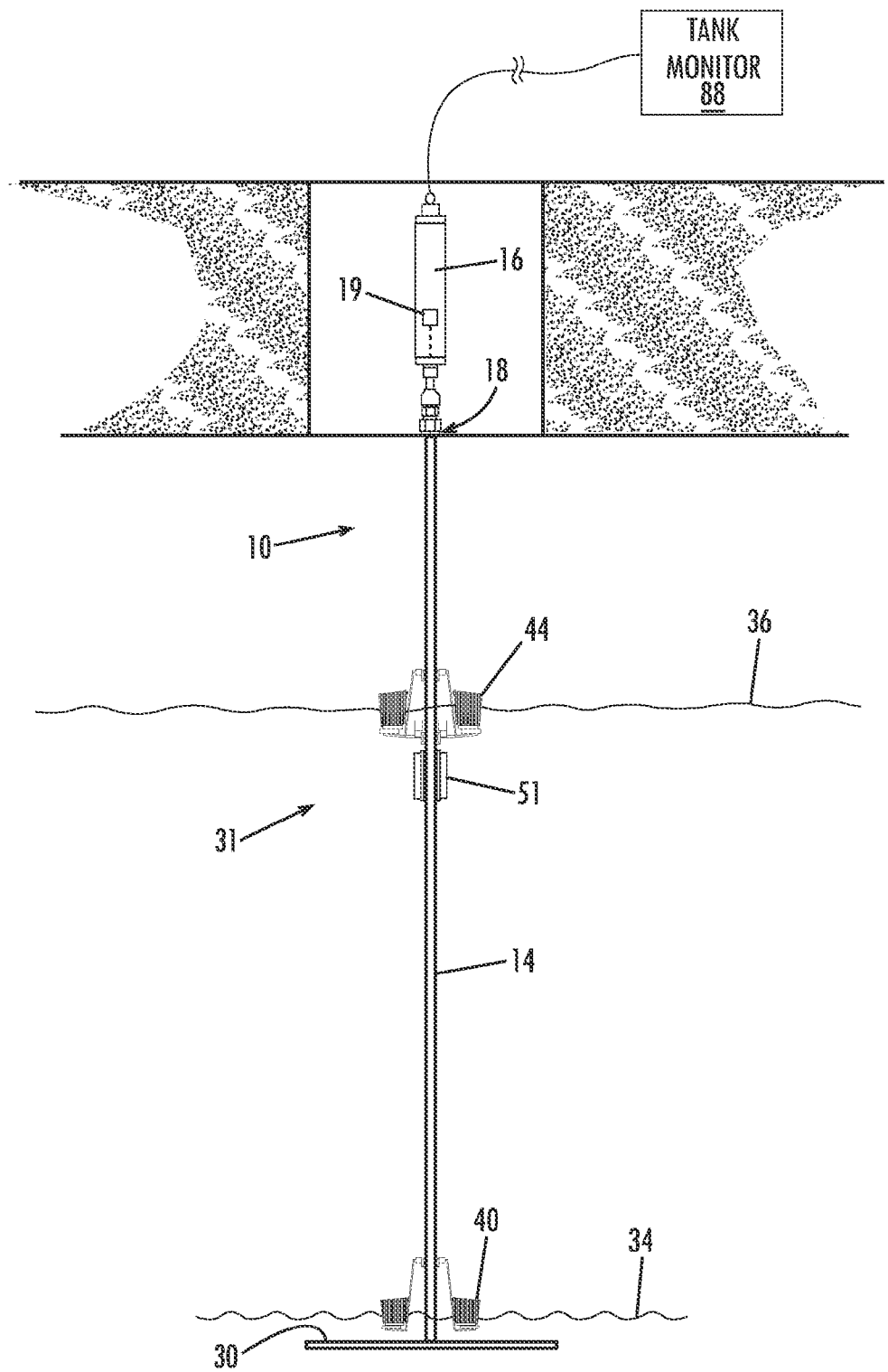
FIG. 2 illustrates a magnetostrictive probe system utilizing a density detector according to a first embodiment of the present invention.
Figure 3:
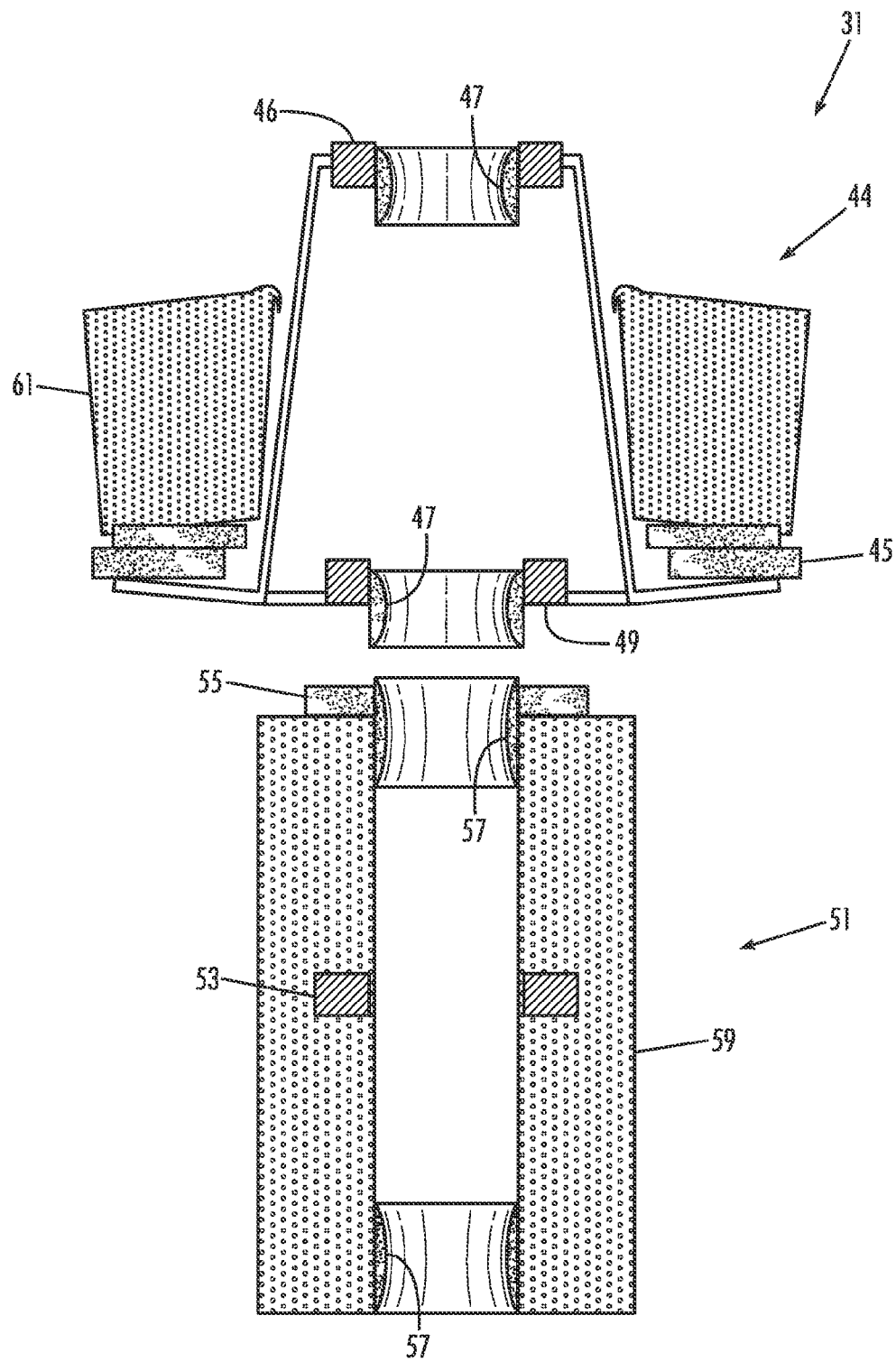
FIG. 3 illustrates the magnetostrictive density detector used in the system of FIG. 2.
Figure 4:
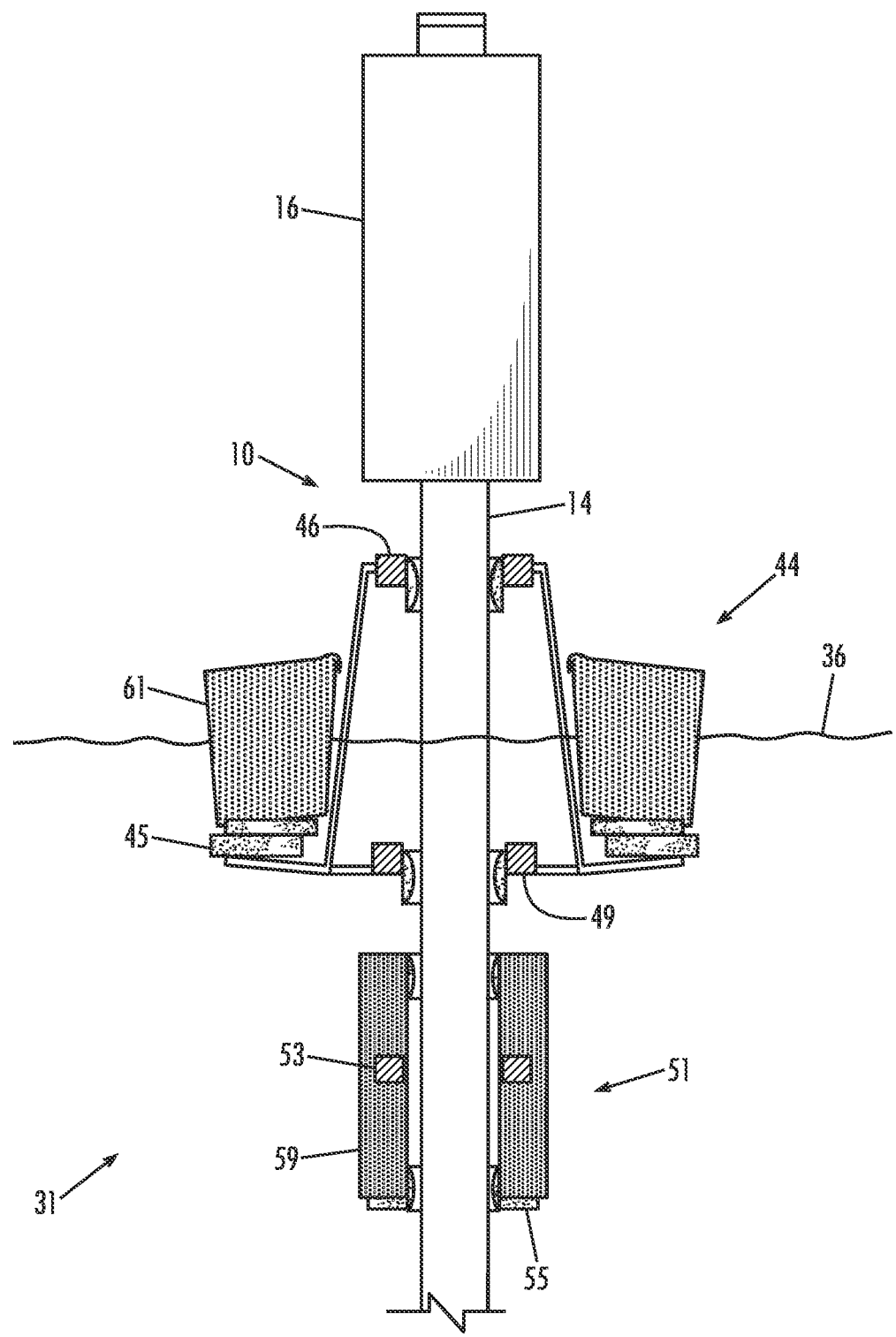
FIG. 4 illustrates the magnetostrictive density detector of FIG. 3 positioned on a probe shaft.

Referring now to FIGS. 2 through 4, a magnetostrictive density detector 31 for determining fuel density at the surface layer of the fuel is shown. Magnetostrictive density detector 31 includes a fuel level float 44 and density float 51, and may be used in combination with a magnetostrictive probe 10 such as shown in FIG. 1. Fuel level float 44 includes ballast 45, a fuel level magnet 46, balancing lips 47, a repulsion magnet 49 and a body 61. In the embodiment shown, repulsion magnet 49 is added to a fuel level float 44 of an existing magnetostrictive probe 10, such as previously discussed. Repulsion magnet 49 is provided in the shown embodiment because fuel level magnet 46 is positioned on an upper portion of fuel level float 44, thereby limiting its ability to interact with density float 51, as discussed in greater detail below. Balancing lips 47 ensure that fuel level float 44 is free to move vertically along probe shaft 14 as the fuel level 36 within the tank changes.

Density float 51 includes a density magnet 53, balancing lips 57, ballast 55 and a body 59. Density magnet 53 is positioned on density float 51 such that adequate magnetic repulsion forces are present between repulsion magnet 49 of fuel level float 44 and density magnet 53 of density float 51. Similarly to balancing lips 47 of fuel level float 44, balancing lips 57 ensure that density float 51 is free to move along probe shaft 14 as the fuel level 36 and density of the fuel change. Also similar to fuel level float 44, ballast 55 is provided and may be changed as necessary such that the buoyancy of density float 51 may be adjusted as necessary, as determined by the fluid in which it will be floating.

Figure 5:
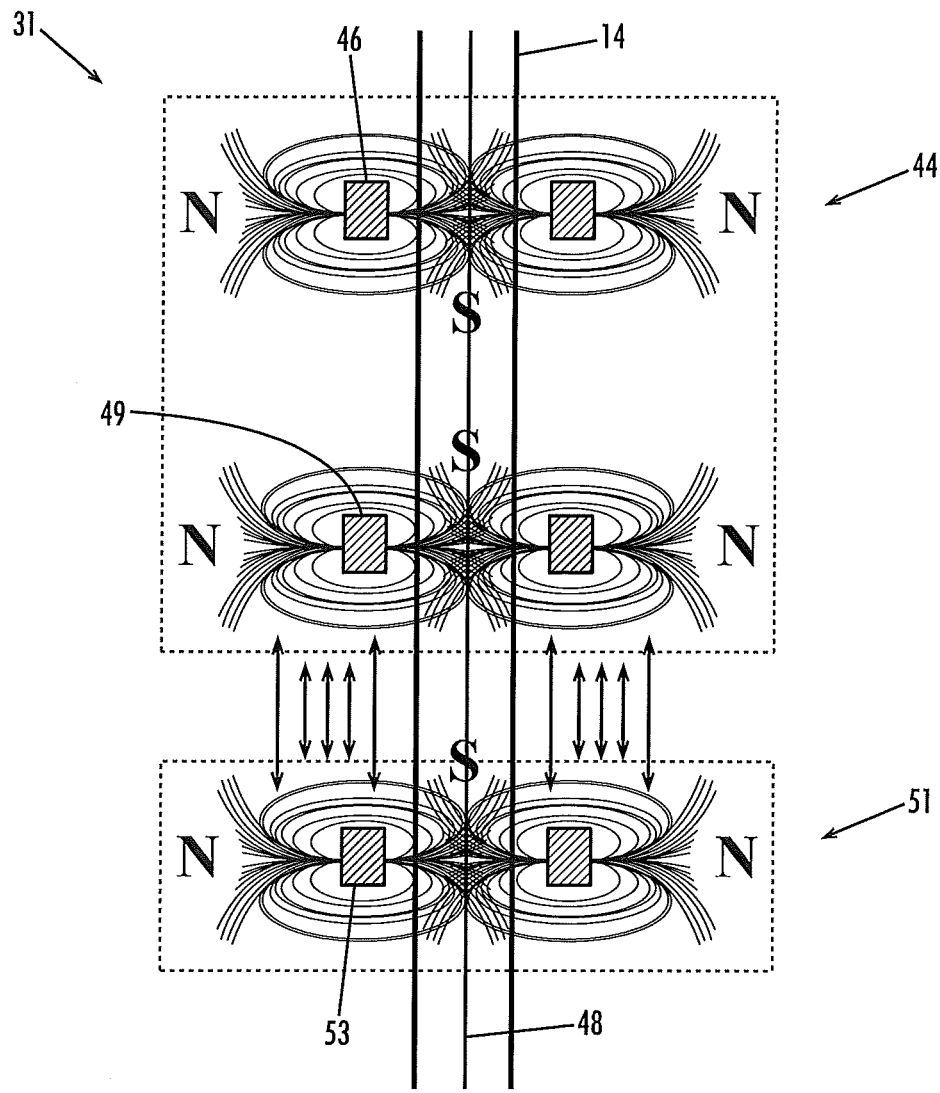
FIG. 5 is a schematic of the magnetostrictive density detector of FIG. 3, illustrating the principle of magnetic repulsion found in the detector.

Referring additionally to FIG. 5, the determination of fuel density by magnetostrictive density detector 31 is based on the effects of magnetic repulsion forces between repulsion magnet 49 positioned on fuel level float 44 and density magnet 53 positioned on density float 51. In short, magnetic repulsion forces generated between repulsion magnet 49 and density magnet 53 will affect the position of density float 51 relative to fuel level float 44, or more specifically, the position of density magnet 53 relative to repulsion magnet 49 along magnetostrictive wire 48 of probe shaft 14.

For the surface layer magnetostrictive density detector 31, density float 51 is calibrated such that it is less buoyant than fuel level float 44 in the fluids for which the detection of density changes is desired. As well, density float 51 is preferably less massive than fuel level float 44 such that the position of density float 51 along probe shaft 14 will change as the fuel density changes but the position of fuel level float 44 will be relatively unaffected. As such, fuel level float 44 and density float 51 are designed such that density float 51 is most affected by the magnetic repulsion forces that exist between repulsion magnet 49 and density magnet 53. Note, however, that density magnet 53 of density float 51 exerts an upward force on fuel level float 44. As such, it may be necessary to adjust the amount of ballast 45 on fuel level float 44 in order to maintain the desired amount of buoyancy and, therefore, accurate fuel level measurement by fuel level magnet 46.

As is known, the vertical position of a float disposed within a fluid will be altered as the density of the fluid changes. For example, as the density of the fluid increases, the float will rise, and as the density decreases, the float will move lower in the fluid. As such, when fuel level float 44 and density float 51 are placed in fuel, the less-massive density float 51 will be repelled by fuel level float 44 due to magnetic repulsion forces between repulsion magnet 49 and density magnet 53, and density float 51 will be made to sink deeper into the fuel as the fuel density decreases. Density magnet 53 will move lower in the fuel along probe shaft 14 until the repulsion forces between the magnets can no longer overcome the buoyant force exerted on density float 51 by the fuel. When the opposing forces null and density float 51 reaches equilibrium, it levitates at a constant position relative to probe shaft 14 and, therefore, magnetostrictive wire 48. The distance at which repulsion magnet 49 and density magnet 53 are separated when at equilibrium in a fluid of known density is a log function of the magnetic repulsion forces. As such, using the previously discussed magnetostrictive probe 10 as shown in FIG. 1, the separation distance between repulsion magnet 49 and density magnet 53 can be determined and a formula derived to determine the fuel density at the surface of the fuel.

Figure 6:
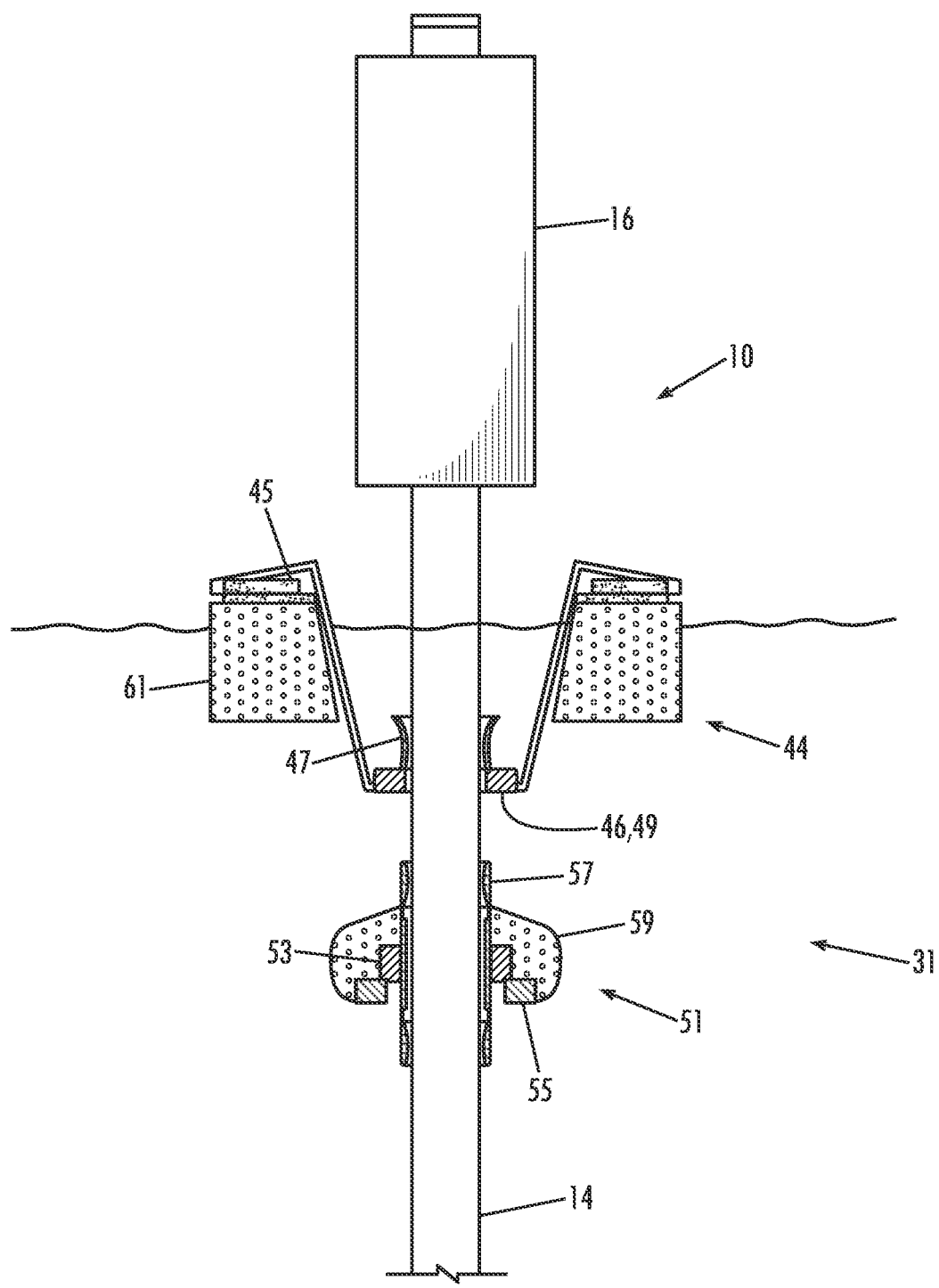
FIG. 6 illustrates a magnetostrictive density detector according to a second embodiment of the present invention.
Figure 7:
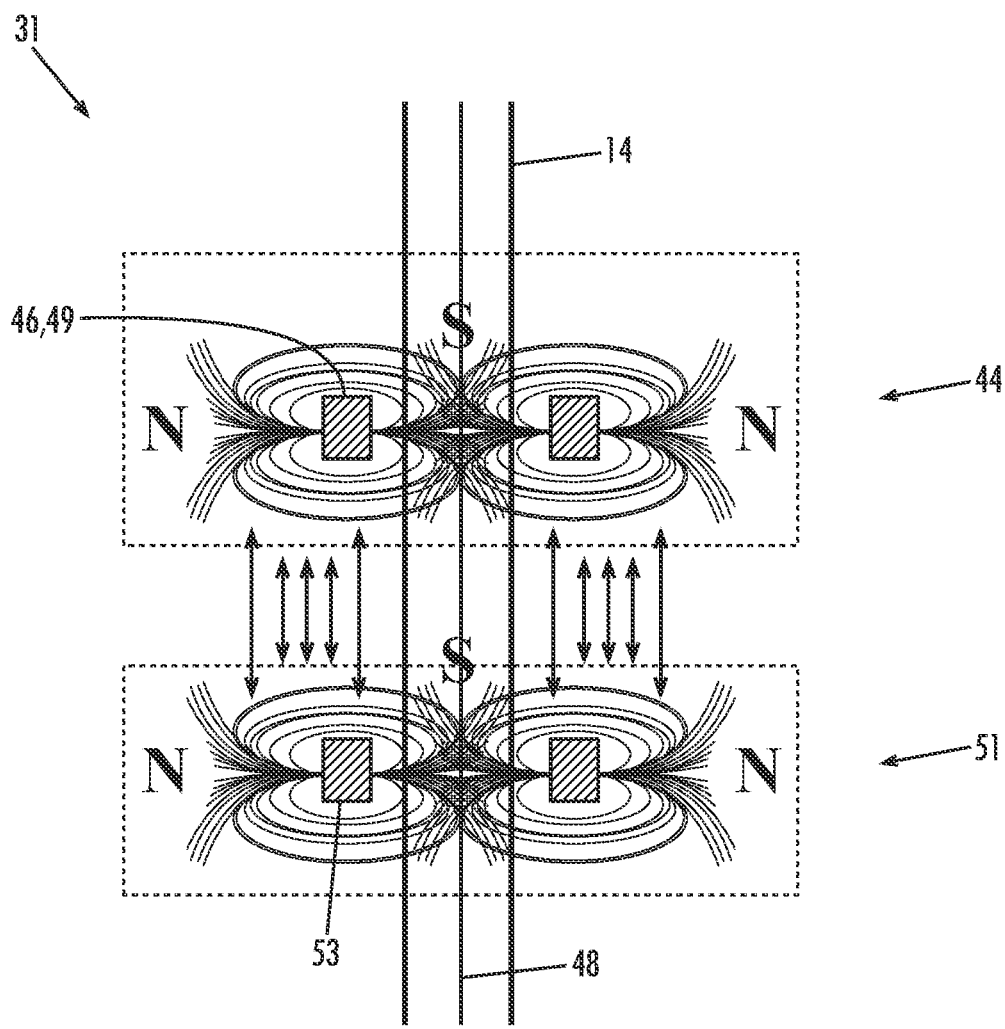
FIG. 7 is a schematic of the magnetostrictive density detector of FIG. 6, illustrating the principle of magnetic repulsion found in the detector.

Referring now to FIGS. 6 and 7, an alternate embodiment of a magnetostrictive density detector 31 for determining surface layer fuel densities is shown. Magnetostrictive density detector 31 operates similarly to the density detector as shown in FIGS. 2 through 5, with the exception that fuel level magnet 46 also functions as a repulsion magnet 49. More specifically, in contrast to the previously discussed embodiment, fuel level magnet 46 is positioned on a bottom portion of fuel level float 44 such that it is disposed within the fuel. As such, it is in close proximity to density float 51 and therefore generates adequate magnetic repulsion forces with density magnet 53 such that it provides the functionality of the repulsion magnet 49 discussed with regard to the embodiment of density detector 31 shown in FIGS. 2 through 5. Other than this difference, the present embodiment of magnetostrictive density detector 31 functions almost identically to the previously discussed embodiment. As such, the previous description of magnetostrictive density detector 31, as shown in FIGS. 2 through 5, applies to the present embodiment and will not be repeated here.

Figure 8:
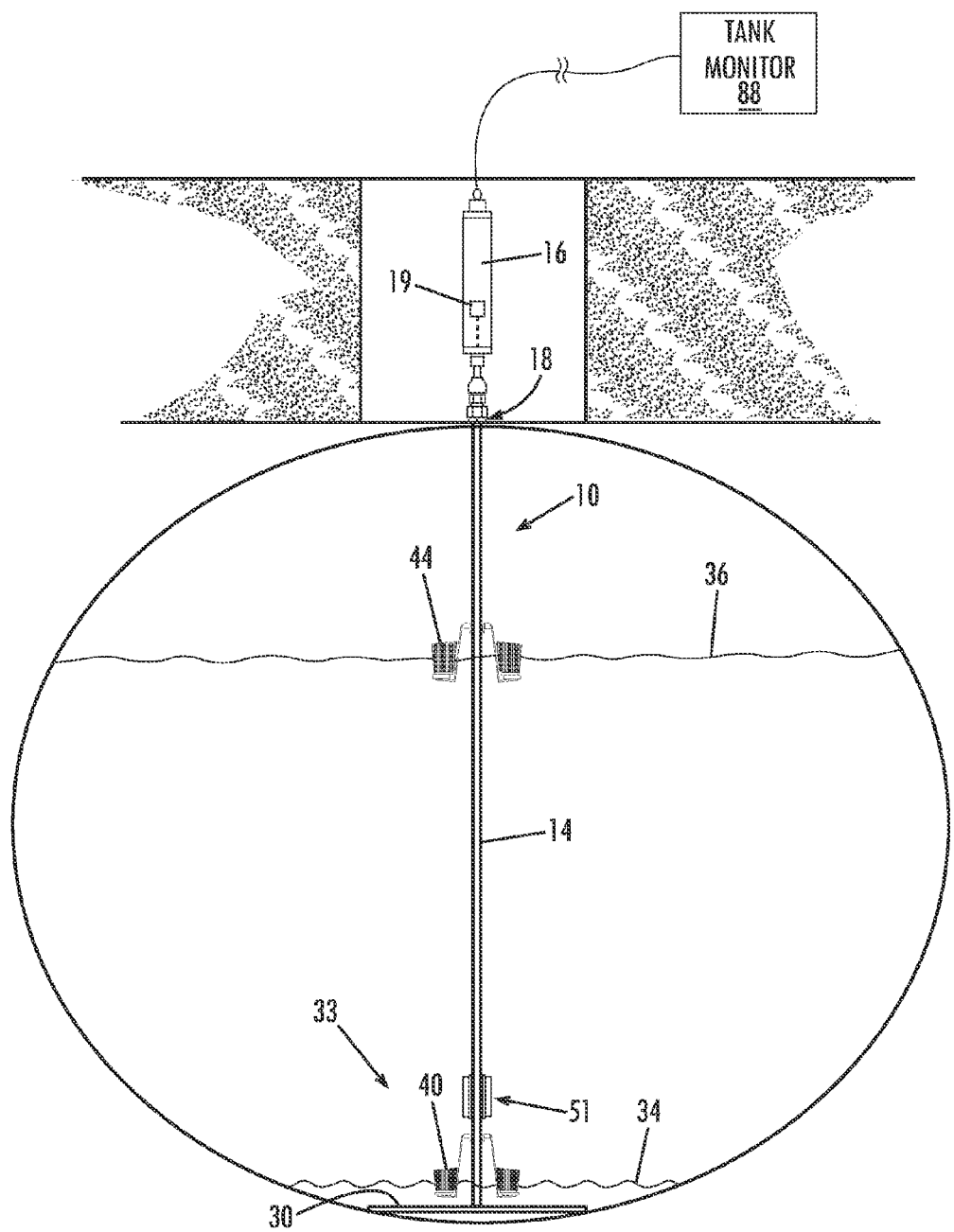
FIG. 8 illustrates a magnetostrictive probe system utilizing a density detector according to a third embodiment of the present invention.
Figure 9:
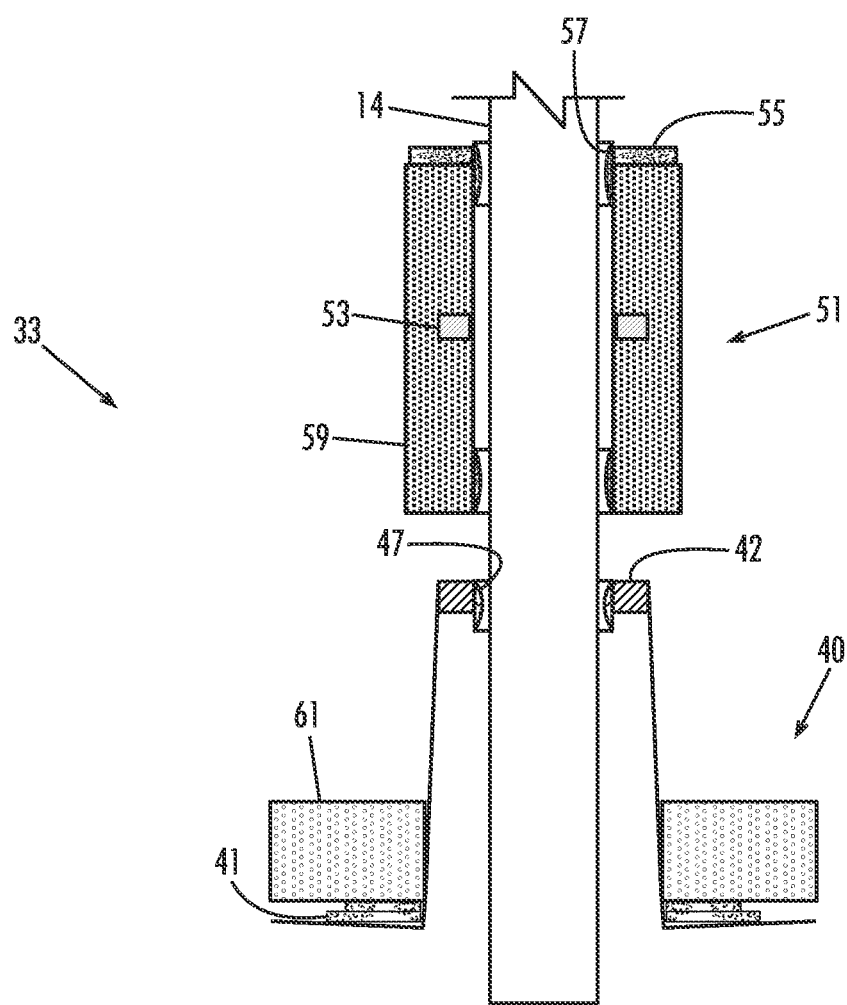
FIG. 9 illustrates the magnetostrictive density detector used in the system of FIG. 8.

Referring now to FIGS. 8 and 9, a magnetostrictive density detector 33 for determining fuel density at a water layer 34 within the fuel is shown. Magnetostrictive density detector 33 includes a water level float 40 and density float 51, and is used in combination with a magnetostrictive probe 10 shown in FIG. 1. Water level float 40 includes ballast 41, a water level magnet 42, balancing lips 47, and a body 61. Balancing lips 47 ensure that water level float 40 is free to move along probe shaft 14 as the water-fuel interface 34 within the tank changes.

Density float 51 includes a density magnet 53, balancing lips 57, ballast 55 and a body 59. Density magnet 53 is positioned on density float 51 such that adequate magnetic repulsion forces are present between repulsion magnet 42 of water level float 40 and density magnet 53 of density float 51. Similarly to balancing lips 47 of water level float 40, balancing lips 57 ensure that density float 51 is free to move along probe shaft 14 as the water level 34 and density of the fuel change. Also similar to water level float 40, ballast 55 is provided and may be changed such that the buoyancy of density float 51 may be adjusted as necessary as determined by the fluid in which it will be floating.

Figure 10:
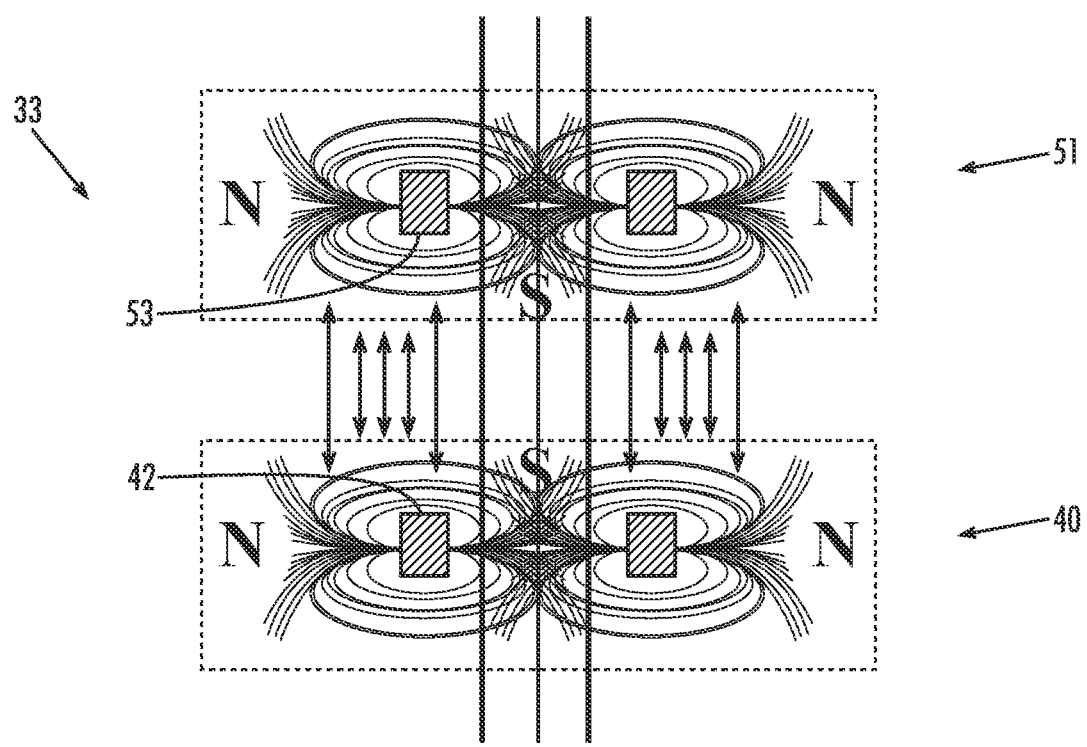
FIG. 10 is a schematic of the magnetostrictive density detector of FIG. 9, illustrating the principle of magnetic repulsion found in the detector.

Referring additionally to FIG. 10, the determination of fuel density by magnetostrictive density detector 33 is based on the effects of magnetic repulsion forces between water level magnet 42 (also functioning as a repulsion magnet) positioned on water level float 40 and density magnet 53 positioned on density float 51. In short, magnetic repulsion forces generated between water level magnet 42 and density magnet 53 will affect the position of density float 51 relative to water level float 40, or more specifically, the position of density magnet 53 relative to water level magnet 42 along magnetostrictive wire 48 of probe shaft 14.

For the water layer magnetostrictive density detector 33, density float 51 is calibrated such that it is more buoyant than water level float 40 in the fluids for which the detection of density changes is desired. As well, density float 51 is preferably less massive than water level float 40 such that the position of density float 51 along probe shaft 14 will change as the fuel density changes but the position of water level float 40 will be relatively unaffected. As such, water level float 40 and density float 51 are designed such that density float 51 is most affected by the magnetic repulsion forces that exist between water level magnet 42 and density magnet 53. Note, however, that density magnet 53 of density float 51 will be exerting a downward force on water level float 40. As such, it may be necessary to adjust the amount of ballast 41 on water level float 40 in order to maintain the desired amount of buoyancy and, therefore, accurate water level measurement by water level magnet 42.

As is known, the vertical position of a float disposed within a fluid will be altered as the density of the fluid changes. For example, as the density of the fluid increases, the float will rise, and as the density decreases, the float will move lower in the fluid. As such, when water level float 40 and density float 51 are placed in fuel, the less-massive density float 51 will be repelled by water level float 40 due to magnetic repulsion forces between water level magnet 42 and density magnet 53, and density float 51 will be made to rise further in the fuel. Density magnet 53 will move upwardly in the fuel along probe shaft 14 until the repulsion forces between the magnets can no longer overcome the ballast force exerted on density float 51 by its weight. When the opposing forces null and density float 51 reaches equilibrium, it levitates at a constant position relative to probe shaft 14 and, therefore, magnetostrictive wire 48. The distance at which water level magnet 42 and density magnet 53 are separated when at equilibrium in a fluid of known density is a log function of the magnetic repulsion forces. As such, using the previously discussed magnetostrictive probe 10 as shown in FIG. 1, the separation distance between water level magnet 42 and density magnet 53 can be determined and a formula derived to determine the fuel density at the surface of the fuel.

Figure 11:
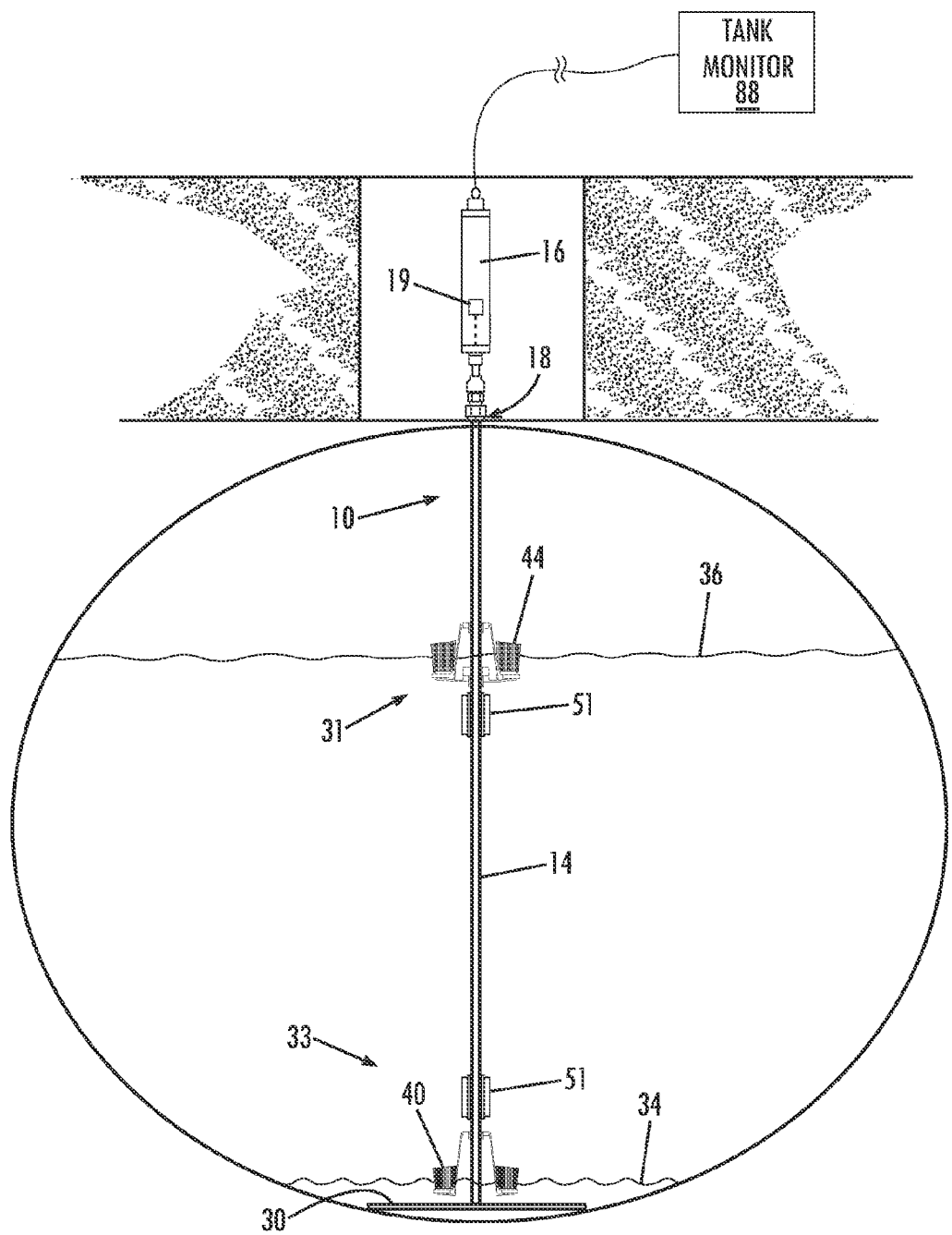
FIG. 11 is a fourth embodiment of the present invention that includes the magnetostrictive density detector of FIG. 3 and the magnetostrictive density detector of FIG. 9.

Referring now to FIG. 11, an embodiment of the present invention is shown in which a magnetostrictive density detector 31 as shown in FIG. 3 is used to measure fuel density of the fuel surface layer and a magnetostrictive density detector as shown in FIG. 9 is used to measure fuel density at the water layer. The principles of operation of this combined embodiment are similar to the previous discussion of the noted density detectors 31 and 33, and therefore, those discussions are not repeated here.

Figure 12:
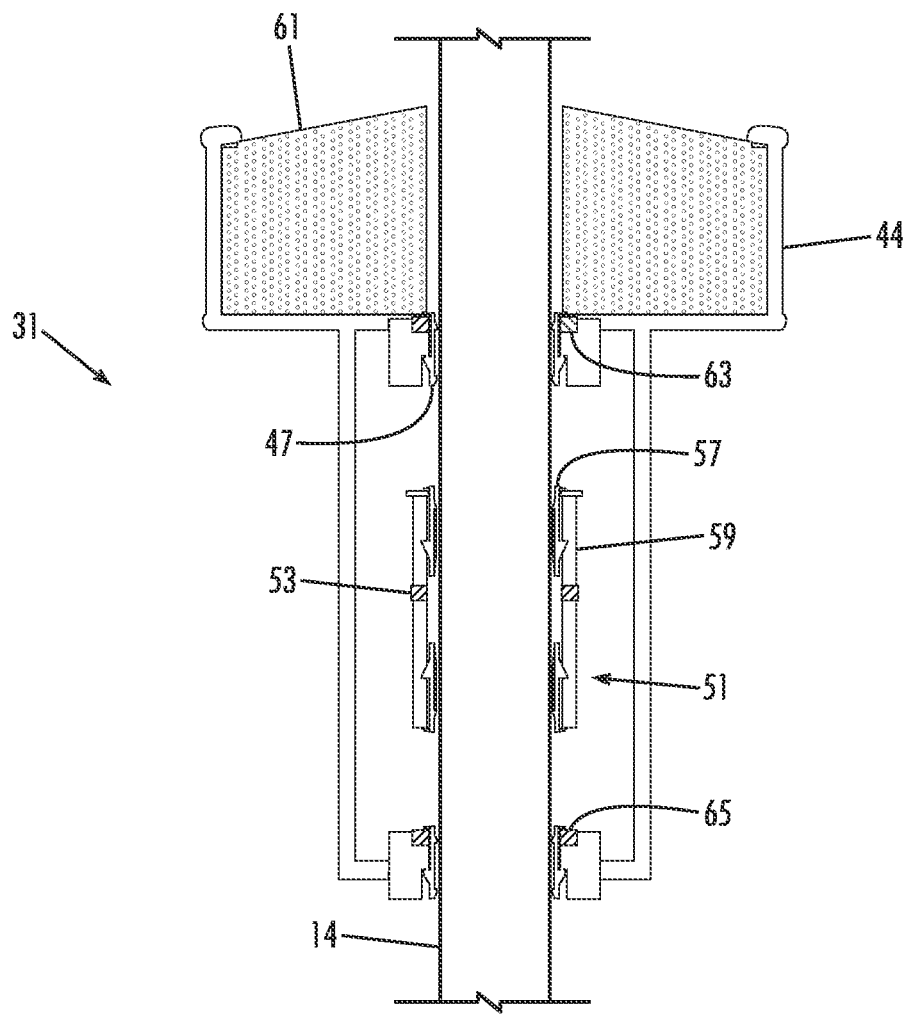
FIG. 12 illustrates a magnetostrictive density detector according to a fifth embodiment of the present invention.
Figure 13:
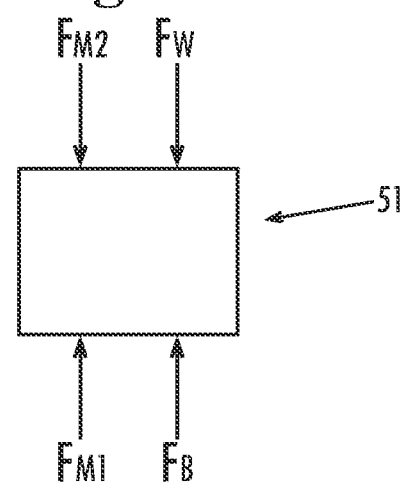
FIG. 13 is a schematic illustrating the forces that define the operating principles of the magnetostrictive density detector of FIG. 12.
Figure 14:
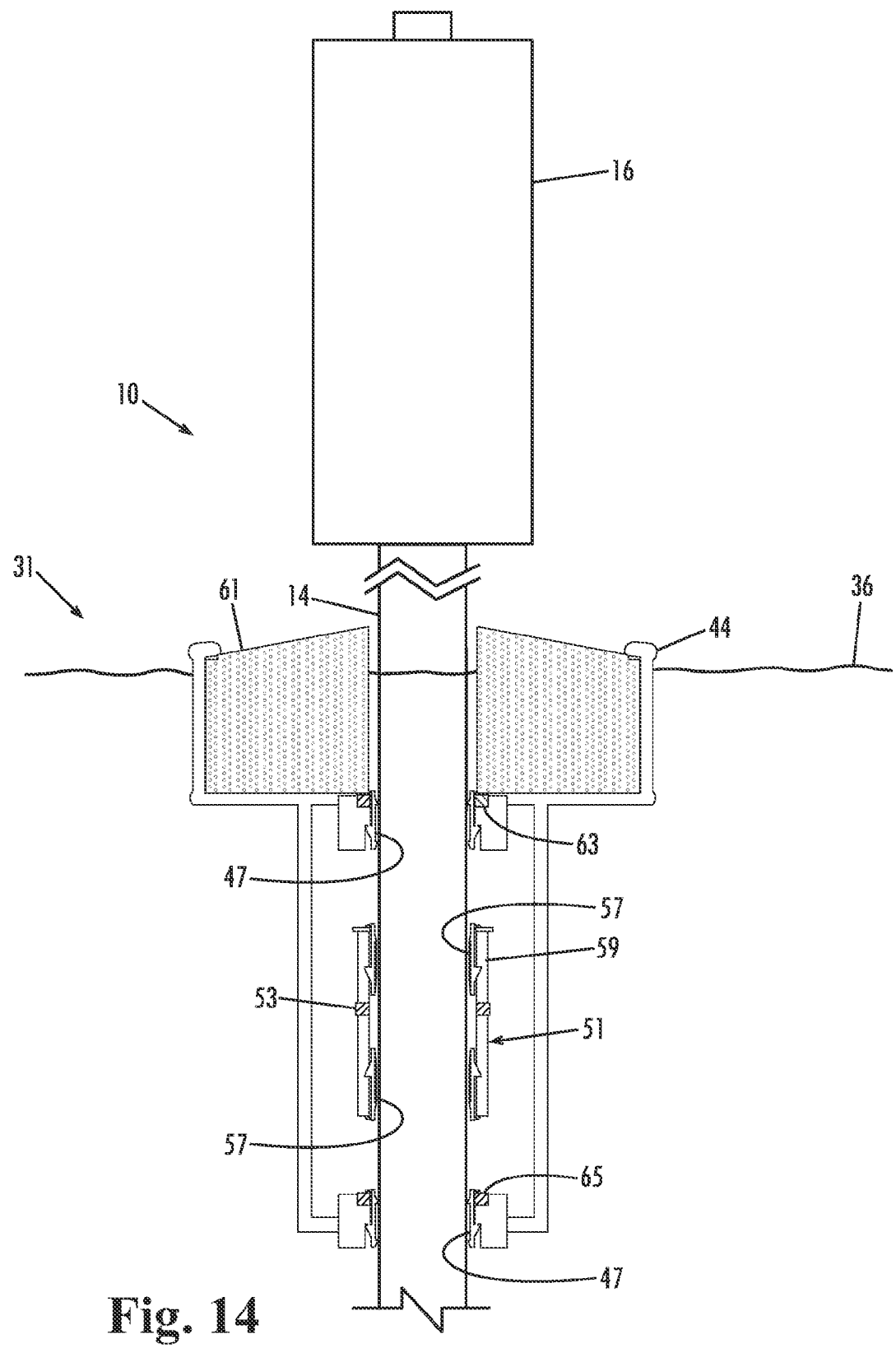
FIG. 14 illustrates the magnetostrictive density detector of FIG. 12.

Referring now to FIGS. 12 through 14, an alternative embodiment of a magnetostrictive density detector 31 for determining fuel density at the surface layer of the fuel is shown. Magnetostrictive density detector 31 includes a fuel level float 44 and an internal density float 51, and is preferably used in combination with a magnetostrictive probe 10 shown in FIG. 1. Fuel level float 44 includes balancing lips 47, a body 61, an upper repulsion magnet 63 and a lower repulsion magnet 65. As shown, upper and lower repulsion magnets 63 and 65 are positioned on opposing portions of the frame of fuel level float 44 such that internal density float is disposed between repulsion magnets 63 and 65. Balancing lips 47 ensure that fuel level float 44 is free to move along probe shaft 14 as fuel level 36 changes within the tank.

As shown, density float 51 includes a density magnet 53, balancing lips 57 and a body 59. Similarly to balancing lips 47 of fuel level float 44, balancing lips 57 ensure that density float 51 is free to move along probe shaft 14 as fuel level 36 and density of the fuel change.

Figure 15:
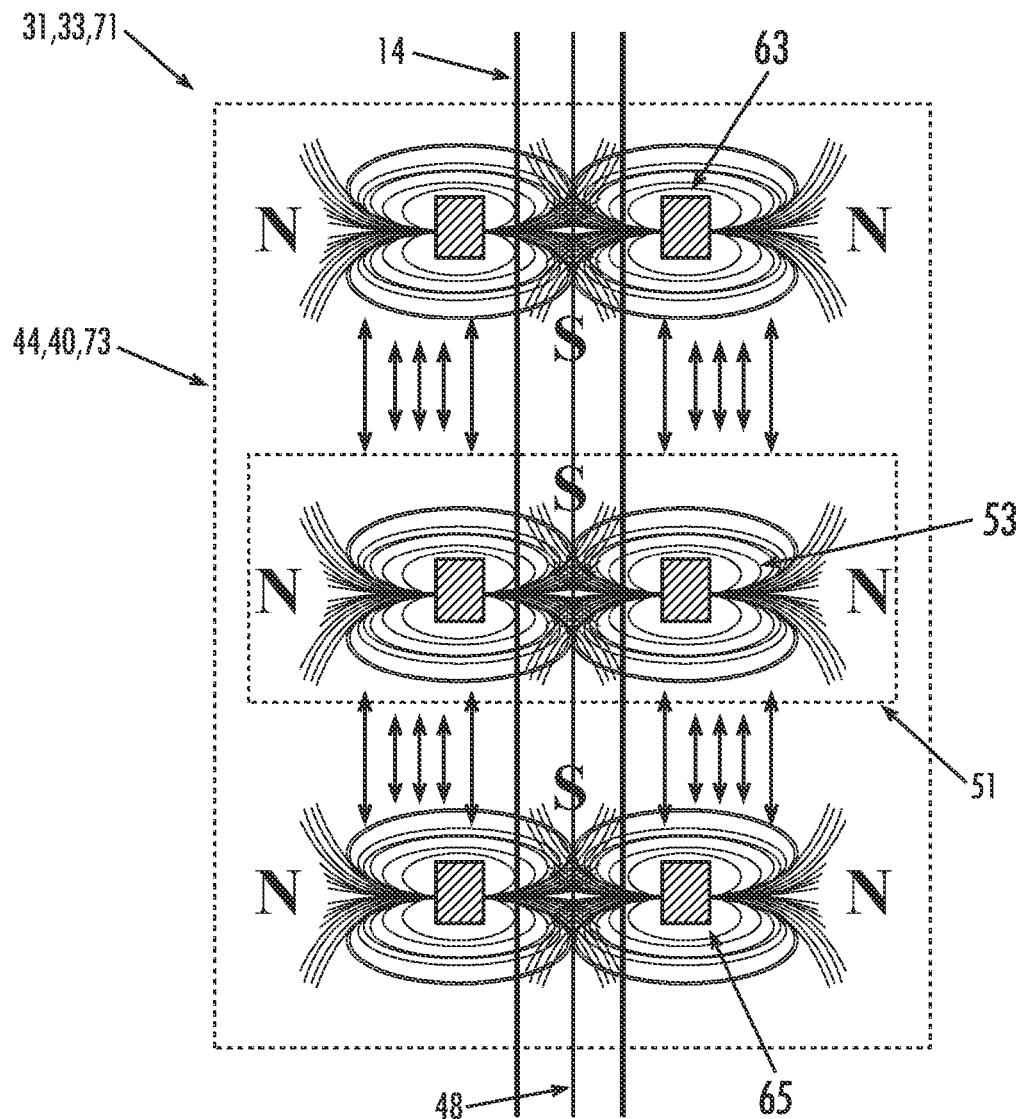
FIG. 15 is a schematic of the magnetostrictive density detector of FIGS. 12, 16 and 17, illustrating the principle of magnetic repulsion found in the detector.

As best seen in FIG. 15, unlike the previously discussed surface layer magnetostrictive density detectors, density float 51 of the present embodiment is subject to magnetic repulsion forces in both the upward and downward directions due to the fact that density float 51 is positioned between upper and lower repulsion magnets 63 and 65, respectively. Referring additionally to FIG. 13, because both the mass and volume of density float 51 are predetermined fixed values, a force balance can be derived to predict the density of the fuel in which magnetostrictive density detector 31 is submerged. More specifically, the force balance equation is:

$$FM1-FM2+FB-FW=0$$

wherein, FM1 is the magnetic repulsion force produced between lower repulsion magnet 65 and density magnet 53; FM2 is the magnetic repulsion force produced between upper repulsion magnet 63 and density magnet 53; FB is upward force produced by the buoyancy of the density float; and FW is the downward force produced by the weight of the density float 51. When fuel level float 44 and density float 51 achieves equilibrium in the fuel, the sum of these forces equals 0.

Figure 18:
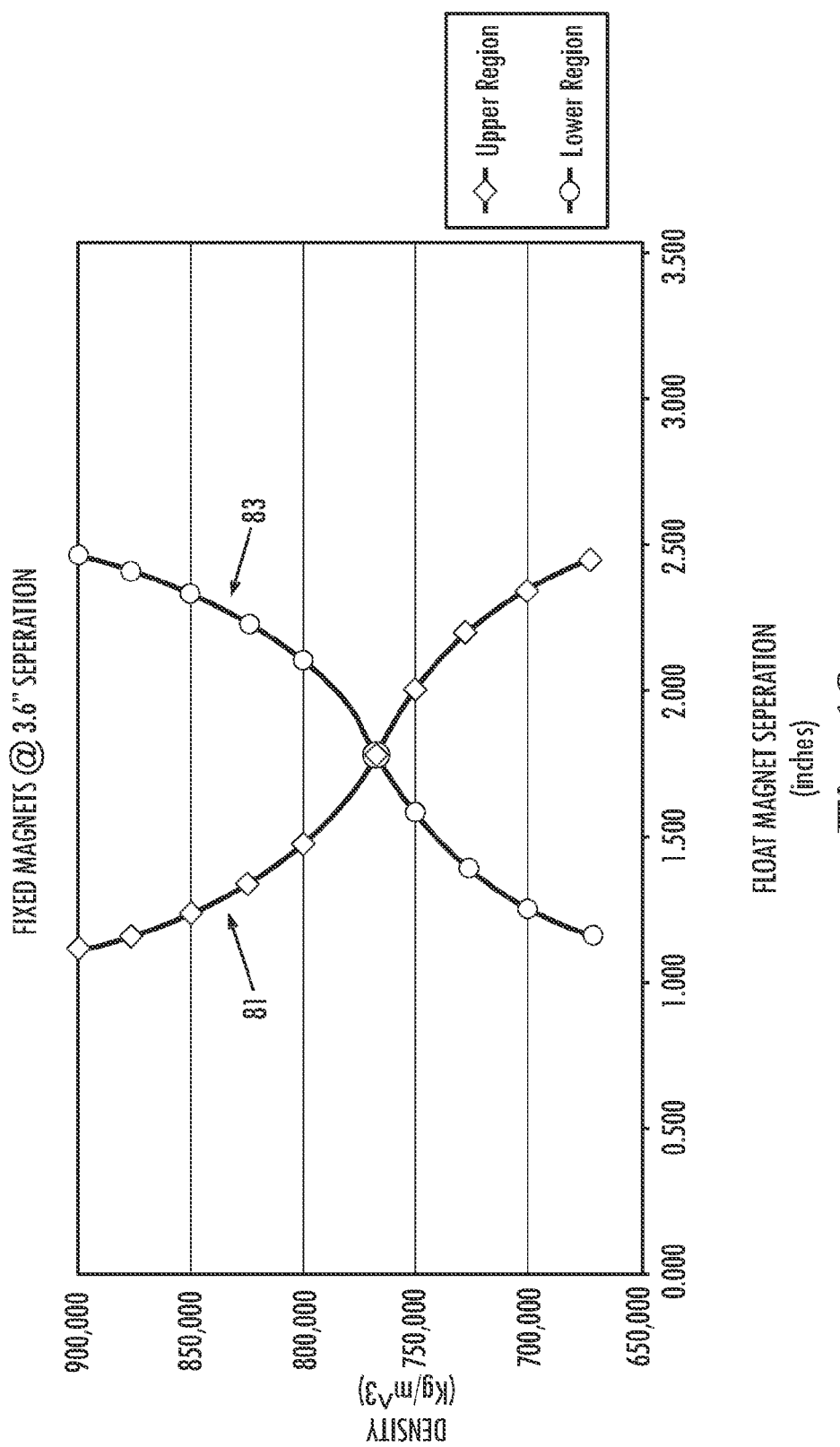
FIG. 18 is a graph illustrating the representative measurements of the distances between the magnets of the density detector of FIG. 12 for varying fuel densities.

Referring now to FIG. 18, an exemplary graph representing the distances between density magnet 53 and upper and lower repulsion magnets 63 and 65, respectively, for varying fuel densities is shown. To determine a fuel density measurement using magnetostrictive density detector 31, the distance between upper repulsion magnet 63 and density magnet 53 (line 81 on the graph) and the distance between lower repulsion magnet 65 and density magnet 53 (line 83 on the graph) is measured. These two distances are measured using the methods and algorithms previously discussed with regard to magnetostrictive probe 10 as shown in FIG. 1. Note, as would be expected, the graph shows that as the fuel density goes up, density float 51 rises relative to fuel level float 44 and the distance from upper repulsion magnet 63 to density magnet 53 decreases as the distance from lower repulsion magnet 65 to density magnet 53 increases. The converse is shown for when fuel density goes down.

The relationship between the displacement of density float 51 and the density of the fuel depends on four factors: the fixed distance between upper repulsion magnet 63 and lower repulsion magnet 65; the material density of density float 51; the volume of density float 51; and the strength of the magnets used. More specifically, the greater the distance between upper repulsion magnet 63 and lower repulsion magnet 65, the greater the resolution that the fuel density measurement will have. However, having too great a distance between upper and lower repulsion magnets 63 and 65 may adversely affect the ability to measure low fuel levels in the tank because, the greater the separation, the greater the length of fuel level float 44. Next, the density of density float 51 determines the center of the range of fuel densities that density detector 31 can measure. Preferably, the density of density float 51 is determined by the average density of the fuel to be measured. Next, the volume of density float 51 is important because the smaller the float, the larger the density range that can be measured. However, a larger density float gives more stable measurements. Lastly, the stronger the magnets that are used in density detector 31, the larger the measurable density range becomes and the more stable the system becomes. By varying these four factors, the magnetostrictive density detector 31 can be designed to cover the desired range of densities for a given fluid.

Figure 16:
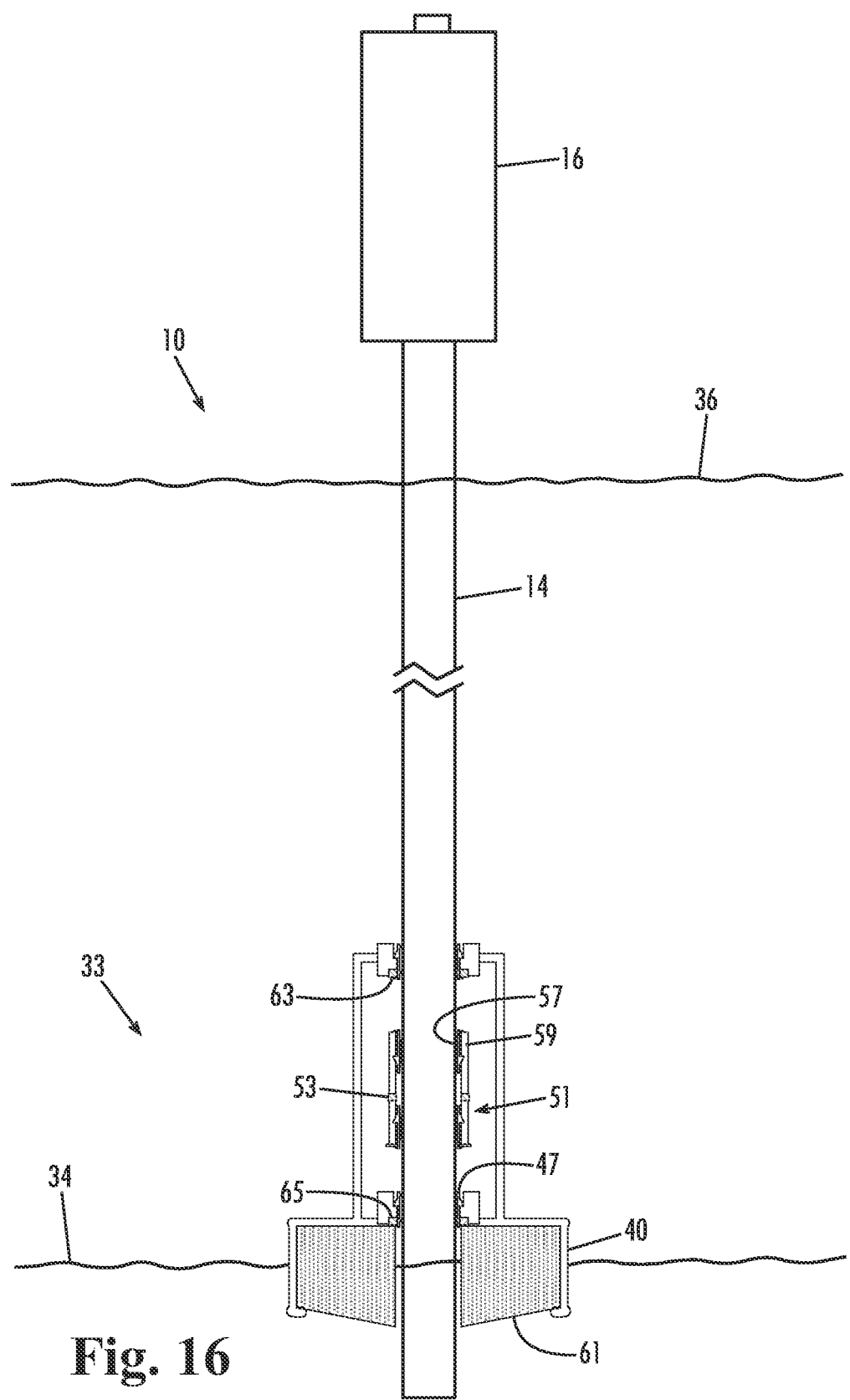
FIG. 16 is a magnetostrictive density detector according to a sixth embodiment of the present invention.

Referring now to FIG. 16, an alternative embodiment of a magnetostrictive density detector 33 for determining fuel density at the water layer of the fuel is shown. Magnetostrictive density detector 33 includes a water level float 40 and an internal density float 51, and is preferably used in combination with a magnetostrictive probe 10 shown in FIG. 1. Water level float 40 includes balancing lips 47, a body 61, an upper repulsion magnet 63 and a lower repulsion magnet 65. As shown, upper and lower repulsion magnets 63 and 65 are positioned on opposing portions of the frame of water level float 40 such that internal density float 51 is disposed between repulsion magnets 63 and 65. Balancing lips 47 ensure that water level float 40 is free to move along probe shaft 14 as water level 34 changes within the tank.

As shown, density float 51 includes a density magnet 53, balancing lips 57 and a body 59. Similarly to balancing lips 47 of water level float 40, balancing lips 57 ensure that density float 51 is free to move along probe shaft 14 as the fuel level and density of the fuel change. The principles of operation of water level density detector 33 are the same as those previously discussed with regard to surface layer density detector 31, as shown in FIG. 12. As such, that discussion is not repeated here.

Figure 17:
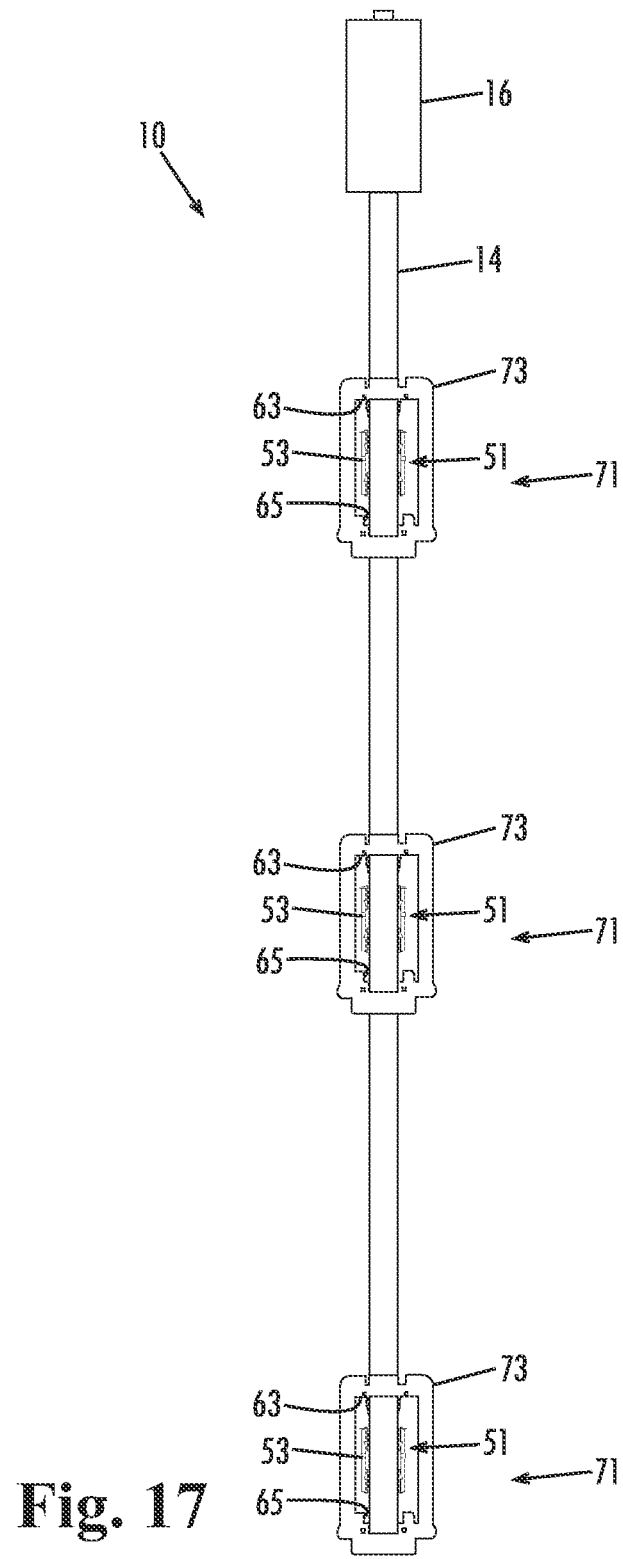
FIG. 17 illustrates a magnetostrictive density detector in accordance with a seventh embodiment of the present invention.

Referring now to FIG. 17, a magnetostrictive density detector 71 for determining fuel density at a desired location along a magnetostrictive probe 10 is shown. Magnetostrictive density detector 71 includes a frame 73 and an internal density float 51. Frame 73 is secured to a fixed position on probe shaft 14 of magnetostrictive probe 10 and includes an upper repulsion magnet 63 and a lower repulsion magnet 65. As shown, upper and lower repulsion magnets 63 and 65 are positioned on opposing portions of frame 73 such that internal density float 51 is disposed between repulsion magnets 63 and 65. As such, density magnet 53 of density float 51 is also positioned between upper and lower repulsion magnets 63 and 65. The primary difference in construction between density detector 71 and previously discussed density detectors 31 and 33, as shown in FIG. 14 and FIG. 16, respectively, is that upper and lower repulsion magnets 63 and 65 are secured to probe shaft 14 in a fixed position that does not vary as the fuel level and water level within the tank vary. As such, the previous description of the operation of density detectors 31 and 33 as shown in FIG. 14 and FIG. 16, respectively, is sufficient to describe the operation of fixed density detector 71, and is therefore not repeated here. This embodiment is desirable because it can be used to detect density across the depth of fuel, thus indicating fuel stratification and other such fuel characteristics. In the illustrated embodiment, for example, a plurality of detectors 71 are fixed at spaced-apart locations along probe shaft 14.

Figure 19:
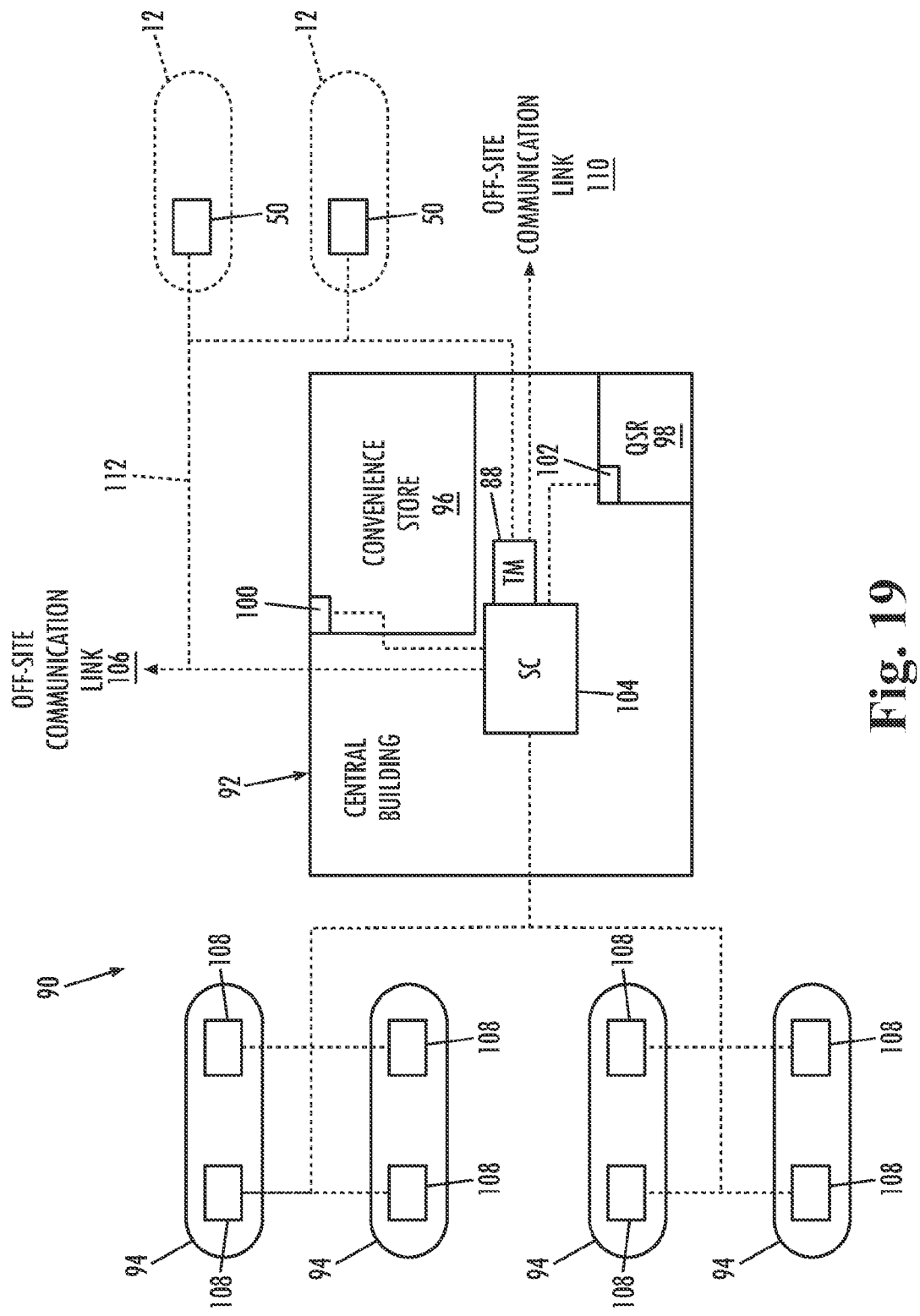
FIG. 19 illustrates a fueling environment incorporating a magnetostrictive density detector in accordance with the present invention.

FIG. 19 illustrates a fueling environment 90 that may incorporate the present invention, and includes the systems and devices that calculate and/or communicate the density of the fuel in the fuel storage tank 12 for the aforementioned purposes. Specifically, the fueling environment 90 may comprise a central building 92 and a plurality of fueling islands 94.

The central building 92 need not be centrally located within the fueling environment 90, but rather is the focus of the fueling environment 90, and may house a convenience store 96 and/or a quick serve restaurant (QSR) 98 therein. Both the convenience store 96 and the quick serve restaurant 98 may include a point of sale 100, 102 respectively. The central building 92 may further house a site controller (SC) 104, which in an exemplary embodiment may be the G-SITE® sold by Gilbarco Inc. of 7300 W. Friendly Avenue, Greensboro, N.C. 27410. The site controller 104 may control the authorization of fueling transactions and other conventional activities as is well understood. The site controller 104 may be incorporated into a point of sale, such as the point of sale 100, if needed or desired. Further, the site controller 104 may have an off-site communication link 106 allowing communication with a remote location for credit/debit card authorization, content provision, reporting purposes, or the like, as needed or desired. The off-site communication link 106 may be routed through the Public Switched Telephone Network (PSTN), the Internet, both, or the like, as needed or desired.

The plurality of fueling islands 94 may have one or more fuel dispensers 108 positioned thereon. The fuel dispensers 108 may be, for example, the ENCORE® dispenser sold by Gilbarco Inc. The fuel dispensers 108 are in electronic communication with the site controller 104 through a LAN or the like.

The fueling environment 90 has one or more fuel storage tanks 12 adapted to hold fuel therein. In a typical installation, fuel storage tanks 12 are positioned underground, and may also be referred to as underground storage tanks. Further, each fuel storage tank 12 has a liquid level probe 50 such as those described herein. The probes 50 report to the tank monitor (TM) 88 associated therewith. Reporting to the tank monitor 88 may be done through a wire-based system, such as an Ethernet LAN, or a wireless system conforming to IEEE standard 802.11g or the like, as needed or desired. The tank monitor 88 may communicate with the fuel dispensers 108 (either through the site controller 104 or directly, as needed or desired) to determine amounts of fuel dispensed, and compare fuel dispensed to current levels of fuel within the fuel storage tanks 12, as needed or desired. In a typical installation, the tank monitor 88 is also positioned in the central building 92, and may be proximate the site controller 104.

The tank monitor 88 may communicate with the site controller 104, and further may have an off-site communication link 110 for leak detection reporting, inventory reporting, or the like. Much like the off-site communication link 106, the off-site communication link 110 may be through the PSTN, the Internet, both, or the like. If the off-site communication link 110 is present, the off-site communication link 106 need not be present, although both links may be present if needed or desired. As used herein, the tank monitor 88 and the site controller 104 are site communicators to the extent that they allow off-site communication and report site data to a remote location.

The present invention may utilize the off-site communication link 110 by forwarding data from the probes 50 to the remote location. This data should preferably be protected from tampering such that the site operator cannot alter the data sent to the remote location through either of the off-site communication links 106 or 110. The data from the probes 50 may be provided to a corporate entity from whom the site operator has a franchise, a governmental monitoring agency, an independent monitoring agency, or the like, as needed or desired. One way to prevent tampering is through an encryption algorithm.

An alternate technique that helps reduce the likelihood of tampering is the use of a dedicated off-site communication link 112, wherein the probes 50 report directly to a location removed from the fueling environment 90. In this manner, the operator of the fueling environment 90 does have not have ready access to the dedicated off-site communication link 112.

For further information on how elements of a fueling environment 90 may interact, reference is made to U.S. Pat. No. 5,956,259, which is hereby incorporated by reference in its entirety. Information about fuel dispensers 108 may be found in U.S. Pat. Nos. 5,734,851 and 6,052,629, which are hereby incorporated by reference in their entireties. For more information about tank monitors 88 and their operation, reference is made to U.S. Pat. Nos. 5,423,457; 5,400,253; 5,319,545; and 4,977,528, which are hereby incorporated by reference in their entireties.

Those skilled in the art will recognize improvements and modifications to the preferred embodiments of the present invention. All such improvements and modifications are considered within the scope of the concepts disclosed herein and the claims that follow.

What is claimed is:

1. A fluid level probe for use in a tank containing a first fluid, comprising:
   a probe shaft including a top end and a bottom end;
   a first float carrying a first magnet, the first float being slidably disposed for movement along the probe shaft and adapted to float at a top surface of the first fluid;
   a second float carrying a first magnet, the second float being slidably disposed for movement along the probe shaft beneath the first float and adapted to float within the first fluid such that there is magnetic repulsion between the first magnet of the first float and the first magnet of the second float; and electronics operative to determine a first distance between the first magnet of the first float and the first magnet of the second float, wherein the mass of the first float is greater than the mass of the second float such that the magnetic repulsion between the first magnet of the first float and the first magnet of the second float has greater effect on the second float.

2. The fluid level probe of claim 1, wherein the electronics are further operative to utilize the first distance to determine a first density of the first fluid adjacent the top surface of the first fluid.

3. The fluid level probe of claim 1, wherein the buoyancy of the first float is greater than the buoyancy of the second float.

4. The fluid level probe of claim 1, wherein the first float further carries a second magnet, the second magnet being positioned such that the first magnet of the first float is disposed between the second magnet and the first magnet of the second float.

5. The fluid level probe of claim 4, wherein a position of the second magnet of the first float relative to the probe shaft is used to determine a position of the top surface of the first fluid relative to the probe shaft.

6. The fluid level probe of claim 1, wherein the first fluid is a fuel and the top surface of the fuel comprises an air-fuel interface.

7. The fluid level probe of claim 6, further comprising:
a third float including a first magnet, the third float being slidably disposed for movement along the probe shaft and adapted to float at a top surface of a second fluid within the tank,
wherein the second fluid is more dense than the fuel.

8. The fluid level probe of claim 7, wherein the second fluid comprises water and the top surface of the water comprises a fuel-water interface.

9. The fluid level probe of claim 7, further comprising:
a fourth float carrying a first magnet, the fourth float being slidably disposed for movement along the probe shaft above the third float and adapted to float within the fuel such that there is magnetic repulsion between the first magnet of the third float and the first magnet of the fourth float.

10. A fluid level probe for use in a tank containing a first fluid and a second fluid forming an interface therebetween, comprising:
a probe shaft including a top end and a bottom end;
a first float carrying a first magnet, the first float being slidably disposed for movement along the probe shaft and adapted to float at the interface between the first fluid and the second fluid;
a second float carrying a first magnet, the second float being slidably disposed for movement along the probe shaft above the first float and adapted to float within the first fluid such that there is magnetic repulsion between the first magnet of the first float and the first magnet of the second float; and
electronics operative to determine a first distance between the first magnet of the first float and the first magnet of the second float,
wherein the mass of the first float is greater than the mass of the second float such that the magnetic repulsion between the first magnet of the first float and the first magnet of the second float has greater effect on the second float.

11. The fluid level probe of claim 10, wherein the electronics are further operative to utilize the first distance to determine a first density of the first fluid adjacent the interface between the first fluid and the second fluid.

12. The fluid level probe of claim 10, wherein the buoyancy of the second float is greater than the buoyancy of the first float.

13. The fluid level probe of claim 10, wherein a position of the first magnet of the first float relative to the probe shaft is used to determine a position of the interface between the first fluid and the second fluid.

14. The fluid level probe of claim 10, further comprising a third float carrying a first magnet, the third float being slidably disposed about the probe shaft and adapted to float at the top surface of the first fluid within the tank.

15. The fluid level probe of claim 14, wherein the first fluid comprises a fuel and the second fluid comprises water, and the interface further comprises a fuel-water interface.

16. A fluid level probe for use in a tank containing a first fluid, comprising:
a probe shaft including a top end and a bottom end;
a first float carrying a first magnet and a second magnet, the first float being slidably disposed for movement along the probe shaft;
a second float carrying a first magnet, the second float being slidably disposed for movement along the probe shaft between the first magnet and the second magnet of the first float and adapted to float within the first fluid such that there is magnetic repulsion between the first magnet of the first float and the first magnet of the second float and also between the second magnet of the first float and the first magnet of the second float; and
electronics adapted to determine a first density of the first fluid adjacent the second float based on spacing between the first magnet of the first float and the first magnet of the second float and between the second magnet of the first float and the first magnet of the second float.

17. The fluid level probe of claim 16, wherein the magnetic repulsion between the first magnet of the first float and the first magnet of the second float and the magnetic repulsion between the second magnet of the first float and the first magnet of the second float act in opposition to each other on the second float.

18. The fluid level probe of claim 16, wherein the first float is adapted to float at a top surface of the first fluid and a position of one of the first magnet and the second magnet of the first float relative to the probe shaft is used to determine a position of the top surface of the first fluid relative to the probe shaft.

19. The fluid level probe of claim 16, wherein the first float is adapted to float on a top surface of a second fluid within the tank, and the second fluid is more dense than the first fluid such that an interface is formed between the first fluid and the second fluid.

20. The fluid level probe of claim 19, wherein the first fluid comprises fuel and the second fluid comprises water, the top surface of the water comprising a fuel-water interface.

21. The fluid level probe of claim 19, wherein a position of one of the first magnet and the second magnet of the first float is used to determine a position of the top surface of the second fluid relative to the probe shaft.

22. A fluid level probe for use in a tank containing a first fluid, comprising:
a probe shaft including a top end and a bottom end;
a first repulsion magnet and a second repulsion magnet, the first repulsion magnet and the second repulsion magnet being disposed at fixed positions along the probe shaft;
a first float carrying a first magnet, the first float being slidably disposed for movement along the probe shaft between the first repulsion magnet and the second repulsion magnet and adapted to float within the first fluid such that there is magnetic repulsion between the first magnet of the first float and the first repulsion magnet and also between the first magnet of the first float and the second repulsion magnet;

electronics operative to determine at least a first distance between one of the first repulsion magnet and the second repulsion magnet and the first magnet of the first float; and a first frame that is fixedly connected to the probe shaft, wherein the first repulsion magnet and the second repulsion magnet are disposed on a first frame that is fixedly connected to the probe shaft.

23. The fluid level probe of claim 22, wherein the electronics are further operative to determine a first density of the first fluid adjacent the first float based at least in part on the first distance.

24. The fluid level probe of claim 22, wherein the magnetic repulsion between the first magnet of the first float and the first repulsion magnet and the magnetic repulsion between the first magnet of the first float and the second repulsion magnet act in opposition to each other on the first float.

25. The fluid level probe of claim 22, further comprising:

a second frame that is fixedly connected to the probe shaft at a location spaced apart from the first frame;

a third repulsion magnet and a fourth repulsion magnet carried by the second frame, the third repulsion magnet and the fourth repulsion magnet being disposed at fixed positions along the probe shaft; and a second float carrying a first magnet, the second float being slidably disposed for movement along the probe shaft between the third repulsion magnet and the fourth repulsion magnet and adapted to float within the first fluid such that there is magnetic repulsion between the first magnet of the second float and the third repulsion magnet and also between the first magnet of the second float and the fourth repulsion magnet, and wherein the electronics determine at least a first distance between one of the third repulsion magnet and the fourth repulsion magnet and the first magnet of the second float.

26. The fluid level probe of claim 25, wherein the electronics are further operative to determine a second density of the first fluid adjacent the second float based at least in part on the first distance between one of the third repulsion magnet and the fourth repulsion magnet and the first magnet of the second float.

27. The fluid level probe of claim 22, wherein the electronics are further operative to determine a second distance between the other of the first repulsion magnet and the second repulsion magnet and the first magnet of the first float, the first distance and said second distance being utilized by the electronics to determine a first density of the first fluid adjacent the first float.

28. The fluid level probe of claim 25, wherein the electronics are further operative to determine a second distance between the other of the third repulsion magnet and the fourth repulsion magnet and the first magnet of the second float, the first distance and the second distance being utilized by the electronics to determine a second density of the first fluid adjacent the second float.

29. A fluid level probe for use in a tank containing a first fluid, comprising:

a probe shaft including a top end and a bottom end;

a first float carrying a first magnet, the first float being slidably disposed for movement along the probe shaft and adapted to float at a top surface of the first fluid;

a second float carrying a first magnet, the second float being slidably disposed for movement along the probe shaft beneath the first float and adapted to float within the first fluid such that there is magnetic repulsion between the first magnet of the first float and the first magnet of the second float; and electronics operative to determine a first distance between the first magnet of the first float and the first magnet of the second float, wherein the first float further carries a second magnet, the second magnet being positioned such that the first magnet of the first float is disposed between the second magnet and the first magnet of the second float.

* * * * *